(12) United States Patent
Steelman et al.

(10) Patent No.: US 10,245,396 B2
(45) Date of Patent: *Apr. 2, 2019

(54) INHALATION DEVICES AND SYSTEMS AND METHODS INCLUDING THE SAME

(71) Applicant: Cerecor, Inc., Baltimore, MD (US)

(72) Inventors: Peter Wayne Steelman, Charlotte, NC (US); James Edward Flynn, New York, NY (US); John Zeis, San Marcos, CA (US); Karla Worley-Ham, Matthews, NC (US)

(73) Assignee: Cerecor, Inc., Baltimore, MD (US)

( * ) Notice: Subject to any disclaimer, the term of this patent is extended or adjusted under 35 U.S.C. 154(b) by 264 days.

This patent is subject to a terminal disclaimer.

(21) Appl. No.: 15/153,482

(22) Filed: May 12, 2016

(65) Prior Publication Data

US 2017/0021118 A1    Jan. 26, 2017

Related U.S. Application Data

(63) Continuation of application No. 13/862,533, filed on Apr. 15, 2013, now Pat. No. 9,364,622.

(Continued)

(51) Int. Cl.
*A61M 15/00* (2006.01)
*A61M 16/12* (2006.01)
(Continued)

(52) U.S. Cl.
CPC ...... *A61M 15/0088* (2014.02); *A61M 15/009* (2013.01); *A61M 15/0013* (2014.02);
(Continued)

(58) Field of Classification Search
CPC ....... A61D 7/04; A61M 11/00; A61M 11/007; A61M 15/00; A61M 15/0013;
(Continued)

(56) References Cited

U.S. PATENT DOCUMENTS

| 3,802,428 A | 4/1974 | Sherman |
| 4,291,688 A | 9/1981 | Kistler |

(Continued)

FOREIGN PATENT DOCUMENTS

| CN | 101547717 A | 9/2009 |
| EP | 0 957 961 A1 | 11/1999 |

(Continued)

OTHER PUBLICATIONS

Chinese Office Action Corresponding to Chinese Patent Application No. 201380032320.9; dated Jun. 24, 2016; Foreign Text, 7 Pages, English Translation Thereof, 7 Pages.

(Continued)

*Primary Examiner* — Annette Dixon
(74) *Attorney, Agent, or Firm* — Adler Pollock & Sheehan P.C; Michel Morency

(57) ABSTRACT

A collapsible inhalation device for use with a metered dose inhaler (MDI) dispenser includes an outlet end member, an inlet end member and a tubular, pliable, collapsible sleeve member attached at either end to the inlet and outlet members. The outlet end member includes a mouthpiece. The inlet end member includes an inlet port and an MDI dispenser mount structure configured to receive and engage the MDI dispenser. The inhalation device is positionable in each of an open position, wherein the sleeve member defines a chamber, and a closed position, wherein the sleeve member is collapsed and enveloped by the outlet end member and the inlet end member.

20 Claims, 25 Drawing Sheets

Related U.S. Application Data

(60) Provisional application No. 61/771,406, filed on Mar. 1, 2013, provisional application No. 61/636,320, filed on Apr. 20, 2012.

(51) Int. Cl.
    *A61M 16/20* (2006.01)
    *A61M 16/10* (2006.01)

(52) U.S. Cl.
    CPC .... *A61M 15/0016* (2014.02); *A61M 15/0018* (2014.02); *A61M 15/0021* (2014.02); *A61M 15/0023* (2014.02); *A61M 15/0068* (2014.02); *A61M 15/0081* (2014.02); *A61M 15/0086* (2013.01); *A61M 16/20* (2013.01); *A61M 16/209* (2014.02); *A61M 15/008* (2014.02); *A61M 15/0071* (2014.02); *A61M 16/107* (2014.02); *A61M 16/208* (2013.01)

(58) Field of Classification Search
    CPC .......... A61M 15/0015; A61M 15/0016; A61M 15/0018; A61M 15/0021; A61M 15/0023; A61M 15/0086; A61M 15/0088; A61M 15/009; A61M 15/08; A61M 16/00; A61M 16/0048; A61M 16/0078; A61M 16/009; A61M 16/0093; A61M 16/06; A61M 16/0616; A61M 16/08; A61M 16/0816; A61M 16/0825; A61M 16/0833; A61M 16/10; A61M 16/1045; A61M 16/14; A61M 16/16; A61M 16/20; A61M 16/208; A61M 16/209; A61M 2202/0208; A61M 2205/583; B05B 15/068; B65D 83/30; G05D 7/00; G05D 7/01; G05D 7/0113; Y10T 29/49826; A62B 18/02; A62B 9/00; A62B 9/02
    USPC ............ 128/200.12, 200.14, 200.22, 200.23, 128/200.24, 202.28, 203.12, 203.15, 128/203.24, 203.28, 203.29, 204.11, 128/204.18, 204.23, 204.26, 205.13, 128/205.24, 207.14
    See application file for complete search history.

(56) References Cited

U.S. PATENT DOCUMENTS

| | | |
|---|---|---|
| 4,470,412 A | 9/1984 | Nowacki et al. |
| 4,484,577 A | 11/1984 | Sackner et al. |
| 4,706,663 A | 11/1987 | Makiej |
| 4,790,305 A | 12/1988 | Zoltan et al. |
| 4,796,614 A | 1/1989 | Nowacki et al. |
| 4,809,692 A | 3/1989 | Nowacki et al. |
| 4,938,210 A | 7/1990 | Shene |
| 4,940,051 A | 7/1990 | Lankinen |
| 5,012,803 A | 5/1991 | Foley et al. |
| 5,012,804 A | 5/1991 | Foley et al. |
| 5,040,527 A | 8/1991 | Larson et al. |
| 5,042,467 A | 8/1991 | Foley et al. |
| 5,074,294 A | 12/1991 | Chiesi |
| 5,109,840 A | 5/1992 | Daleiden |
| 5,203,323 A | 4/1993 | Tritle |
| 5,304,082 A | 4/1994 | Wolfe |
| 5,318,016 A | 6/1994 | Mecikalski |
| 5,385,140 A | 1/1995 | Smith |
| 5,394,822 A | 3/1995 | Worland |
| 5,427,089 A | 6/1995 | Kraemer |
| 5,477,849 A | 12/1995 | Fry |
| 5,497,765 A | 3/1996 | Praud et al. |
| 5,501,214 A | 3/1996 | Sabo |
| 5,513,626 A | 5/1996 | Hamilton |
| 5,571,246 A | 11/1996 | Alldredge |
| 5,598,593 A | 2/1997 | Wolfe |
| 5,613,489 A | 3/1997 | Miller et al. |
| 5,645,049 A | 7/1997 | Foley et al. |
| 5,685,296 A | 11/1997 | Zdrojkowski |
| 5,724,962 A | 3/1998 | Vidgren et al. |
| 5,809,996 A | 9/1998 | Alldredge |
| 5,816,240 A | 10/1998 | Komesaroff |
| 5,848,588 A | 12/1998 | Foley et al. |
| 5,988,160 A | 11/1999 | Foley et al. |
| 6,026,807 A | 2/2000 | Puderbaugh et al. |
| 6,039,042 A | 3/2000 | Sladek |
| 6,240,917 B1 | 6/2001 | Andrade |
| 6,293,279 B1 | 9/2001 | Schmidt et al. |
| 6,345,617 B1 | 2/2002 | Engelbreth et al. |
| 6,435,177 B1 | 8/2002 | Schmidt et al. |
| 6,463,929 B1 | 10/2002 | Scheuch et al. |
| 6,494,202 B2 | 12/2002 | Farmer |
| 6,550,473 B1 | 4/2003 | Sladek |
| 6,554,808 B1 | 4/2003 | Cook |
| 6,557,549 B2 | 5/2003 | Schmidt et al. |
| 6,595,204 B2 | 7/2003 | Genova et al. |
| 6,595,206 B2 | 7/2003 | Vito |
| 6,604,522 B2 | 8/2003 | Arvidsson et al. |
| 7,107,987 B2 | 9/2006 | Sundaram et al. |
| 7,360,537 B2 | 4/2008 | Snyder et al. |
| 7,404,400 B2 | 7/2008 | Lulla et al. |
| 7,418,962 B1 | 9/2008 | Rao |
| D585,542 S | 1/2009 | Watson et al. |
| 7,562,656 B2 | 7/2009 | Gallem et al. |
| 7,748,385 B2 | 7/2010 | Lieberman |
| 8,074,641 B2 | 12/2011 | Gallem et al. |
| 8,074,642 B2 | 12/2011 | Bruce et al. |
| RE43,174 E | 2/2012 | Schmidt et al. |
| 9,364,622 B2 * | 6/2016 | Steelman .......... A61M 15/0086 |
| 2002/0069870 A1 | 6/2002 | Farmer |
| 2002/0083528 A1 | 7/2002 | Fisher et al. |
| 2003/0028234 A1 | 2/2003 | Miller et al. |
| 2003/0101516 A1 | 6/2003 | Hsu et al. |
| 2003/0150748 A1 | 8/2003 | Crawley |
| 2003/0205226 A1 | 11/2003 | Gallem et al. |
| 2004/0267086 A1 | 12/2004 | Anstadt et al. |
| 2005/0039746 A1 | 2/2005 | Grychowski et al. |
| 2005/0171507 A1 | 8/2005 | Christian et al. |
| 2006/0047341 A1 | 3/2006 | Trieu |
| 2006/0084985 A1 | 4/2006 | Kim |
| 2007/0283954 A1 | 12/2007 | Dhuper et al. |
| 2007/0289590 A1 | 12/2007 | Kreutzmann et al. |
| 2008/0210225 A1 | 9/2008 | Geiger |
| 2011/0132359 A1 | 6/2011 | Poree |
| 2011/0209700 A1 | 9/2011 | Kreutzmann et al. |
| 2011/0232636 A1 | 9/2011 | Von Hollen et al. |
| 2012/0042874 A1 | 2/2012 | Gallem et al. |

FOREIGN PATENT DOCUMENTS

| | | |
|---|---|---|
| EP | 2 179 760 A2 | 4/2010 |
| GB | 2 275 615 A | 9/1994 |
| JP | S 55112535 U | 8/1980 |
| JP | H 05-24042 U | 2/1993 |
| JP | 2000-279518 A | 10/2000 |
| JP | 2003-503117 A | 1/2003 |
| JP | 2010-501224 A | 1/2010 |
| WO | WO 00/33902 A1 | 6/2000 |
| WO | WO 02/092146 A2 | 11/2002 |
| WO | WO 2010/070496 A1 | 6/2010 |
| WO | WO 2012/038861 A1 | 3/2012 |

OTHER PUBLICATIONS

"AeroChamber Plus Flow-Vu Anti-Static Valved Holding Chamber, Mouthpiece, Large Mask" Forest Pharmaceuticals, Inc., RMC 16416 Revision: Jan. 2010 (1 page).

"AeroChamber Plus Flow-Vu Anti-Static Valved Holding Chamber, Small Mask, Medium Mask" Forest Pharmaceuticals, Inc., RMC 16417 Revision: Jan. 2010 (1 page).

"AeroChamber Plus Valved Holding Chamber" Forest Pharmaceuticals, Inc., Retrieved Date: May 6, 2010, From URL: http://www.aerochambervhc.com (3 pages).

(56) References Cited

OTHER PUBLICATIONS

"E-Z Spacer® Collapsible holding chamber for metered-dose inhalers" FSC Laboratories, Inc., FSC 393-11, Rev A, Nov. 2008 (1 page).
Haidl et al., "Inhaled isotonic alkaline versus saline solution and radioaerosol clearance in chronic cough" *European Respiratory Journal* 2000; 16: 1102-1108.
Hsu et al. "Breath-by-breath Delivered Dose Comparison from Three Anti-Static Valved Holding Chambers With Facemasks Under Simulated Use Conditions", Philips Respironics.
Hsu et al. "Evaluation of Delivery Efficiency from Valved Holding Chambers with Facemasks Under Simulated Use Conditions", Retrieved from the internet at URL http://www.healthcare.philips.com/pwc_hc/us_en/homehealth/respiratory_drug_delivery/optichamberdiamond/pdf/RDD_2011_Hsu_et_al_LiteTouch_Facemask_seal.pdf, Date unknown but admitted prior art.
Invitation to Pay Additional Fees in corresponding PCT Application No. PCT/US2013/036936 dated Jun. 27, 2013, 8 Pages.
Nikander et al. In Vitro Comparison of Aerosol Characteristics of HFA Ipratropium Bromide Pressurized Metered Dose Inhaler (pMDI) Formulation from Three Valved Holding Chambers (VHCs), Philips Respironics, Presented at the European Respiratory Society Conference, Sep. 24-28, 2011, Amsterdam, The Netherlands, 1 page.
Notification of Transmittal of the International Search Report and the Written Opinion in corresponding PCT Application No. PCT/US2013/036936 dated Sep. 16, 2013, 17 pages.
Notification Concerning Transmittal of International Preliminary Report on Patentability in corresponding PCT Application No. PCT/US2013/036936 dated Oct. 30, 2014, 12 pages.
"Optichamber® Advantage Valved Holding Chamber" Philips Respironics, Retrieved Date: Oct. 14, 2010, From URL: http://optichamberholdingchamber.respironics.com/default.asp, 5 pages.
"OptiChamber Advantage Valved Holding Chamber" Koninklijke Philips Electronics N.V., Retrieved Date: May 6, 2010, From URL: http://www.healthcare.philips.com/main/homehealth/respiratory_drug_delivery/optichamberholdingchamber/default.wpg, 1 page.
"PARI Granted US Patent for Vortex Holding Chamber" PARI Respiratory Equipment, Inc., News Release, Midlothian, Virginia, Jul. 21, 2009, 1 page.
"PARI in the Americas—The Lower Airways—Home" PARI Respiratory Equipment, Inc., Retrieved Date: May 6, 2010, From URL: http://www.pari.com/pdd.htm, 1 page.
"PARI VORTEX® Non Electrostatic Valved Holding Chamber" PARI Respiratory Equipment, Inc., Retrieved Date: May 6, 2010, From URL: http://www.pari.com/pdd/vortex.htm, 2 pages.
Philips Respironics, "OptiChamber Diamond anti-static valved holding chamber", 2011 Koninklijke Philips Electronics N.V., Retrived from the internet at URL http://www.healthcare.philips.com/pwc_hc/main/homehealth/respiratory_drug_delivery/litetouch/pdf/PR_OCD_AerosolCharacterization_Charts_HI.pdf, 3 pages.
Philips Respironics, "Philips Respironics OptiChamber Diamond anti-static valved holding chamber", 2011 Koninklijke Philips Electronics N.V., Retrieved from the internet at URL http://www.healthcare.philips.com/pwc_hc/main/homehealth/respiratory_drug_delivery/optichamberdiamond/pdf/Intl-PN1091731.pdf, 2 pages.
"Pocket Flow Spacer" Health Enterprise East Ltd., Retrieved Date: Jun. 21, 2010, From URL: http://www.hee.org.uk/Licensing-Opportunities/pocket-flow-spacer.html, 1 page.

"Spacers and holding chambers" Koninklijke Philips Electronics N.V., Retrieved Date: May 6, 2010, From URL: http://www.healthcare.philips.com/main/homehealth/respiratory_drug_delivery/spacers_and_holding_chambers/index.wpd, 1 page.
Von Hollen et al. "Determining the Influence of Washing on the Aerosol Performance of an Anti-Static Valved Holding Chamber" Philips Respironics, Presented at the Association of Asthma Educators Annual Conference, Jul. 22-24, 2011, Denver, Colorado, USA, 1 page.
Von Hollen et al. "Effect of Simulated Facial Movement on the Seal Integrity of a Valved Holding Chamber Mask", Philips Respironics, Presented at the American Thoracic Society International Conference, May 14-19, 2010, New Orleans, LA, USA, 1 page.
Von Hollen et al. "In Vitro Comparison of Aerosol Characteristics of Two Pressurized Metered Dose Inhaler Formulations Commonly Used in COPD", Philips Respironics, Presented at the American Association of Pharmaceutical Scientists Conference, Oct. 23-27, 2011, Washington, DC. USA, 1 page.
Von Hollen et al. "In Vitro Comparison of Aerosol Characteristics of HFA Albuterol Pressurized Metered Dose Inhaler Formulation from Anti-Static Valved Holding Chambers", Philips Respironics, Presented at the American Thoracic Society International Conference, May 13-18, 2011, Denver, CO, USA, 1 page.
Von Hollen et al. In Vitro Comparison of Aerosol Characteristics of H FA Albuterol (Salbutamol) Pressurized Metered Dose Inhaler (pMDI) Formulation from Three Valved Holding Chambers (VHCs), Philips Respironics, Presented at the European Respiratory Society Conference, Sep. 24-28, 2011, Amsterdam, The Netherlands, 1 page.
Von Hollen et al. "Quantifying Facemask Sealing Efficiency when used on a Valved Holding Chamber During Simulated Breathing", Philips Respironics, Presented at the Association of Asthma Educators annual conference, Jul. 31-Aug. 2, 2009, New Orleans, LA, 1 page.
Von Hollen et al., "Comparison of Aerosol Characteristics from Two HFA Pressurized Metered Dose Inhaler Formulations using Anti-Static Valved Holding Chambers", Philips Respironics, Presented at Respiratory Drug Delivery Europe, Berlin, Germany, May 3-6, 2011, (1 page).
Von Hollen et al., "Evaluation of the Aerosol Characteristics of an HFA Fluticasone Propionate Pressurized Metered Dose Inhaler Formulation with Conventional and Anti-Static plastic Valved Holding Chambers", Philips Respironics, Presented at the 18$^{th}$ Congress of International Society for Aerosols in Medicine, Jun. 18-22, 2011, Rotterdam, The Netherlands, (1 page).
Von Hollen et al., "Impact of Flow Rate Change on the Aerosol Characteristics of HFA Albuterol (Salbutamol) Pressurized Metered Dose Inhaler Formulation with an Anti-Static Valved Holding Chamber", Philips Respironics, Presented at the 18$^{th}$ Congress of International Society for Aerosols in Medicine, Jun. 18-22, 2011, Rotterdam, The Netherlands, (1 page).
European Office Action Corresponding to European Patent Application No. 13720185.1 (11 Pages) (dated Nov. 9, 2017).
Chinese Office Action Corresponding to Chinese Patent Application No. 201380032320.9; dated Mar. 10, 2017; Foreign Text, 10 Pages, English Translation Thereof, 11 Pages.
Japanese Office Action Corresponding to Japanese Patent Application No. 2015-507142; dated Dec. 9, 2016; Foreign Text, 6 Pages, English Translation Thereof, 5 Pages.

* cited by examiner

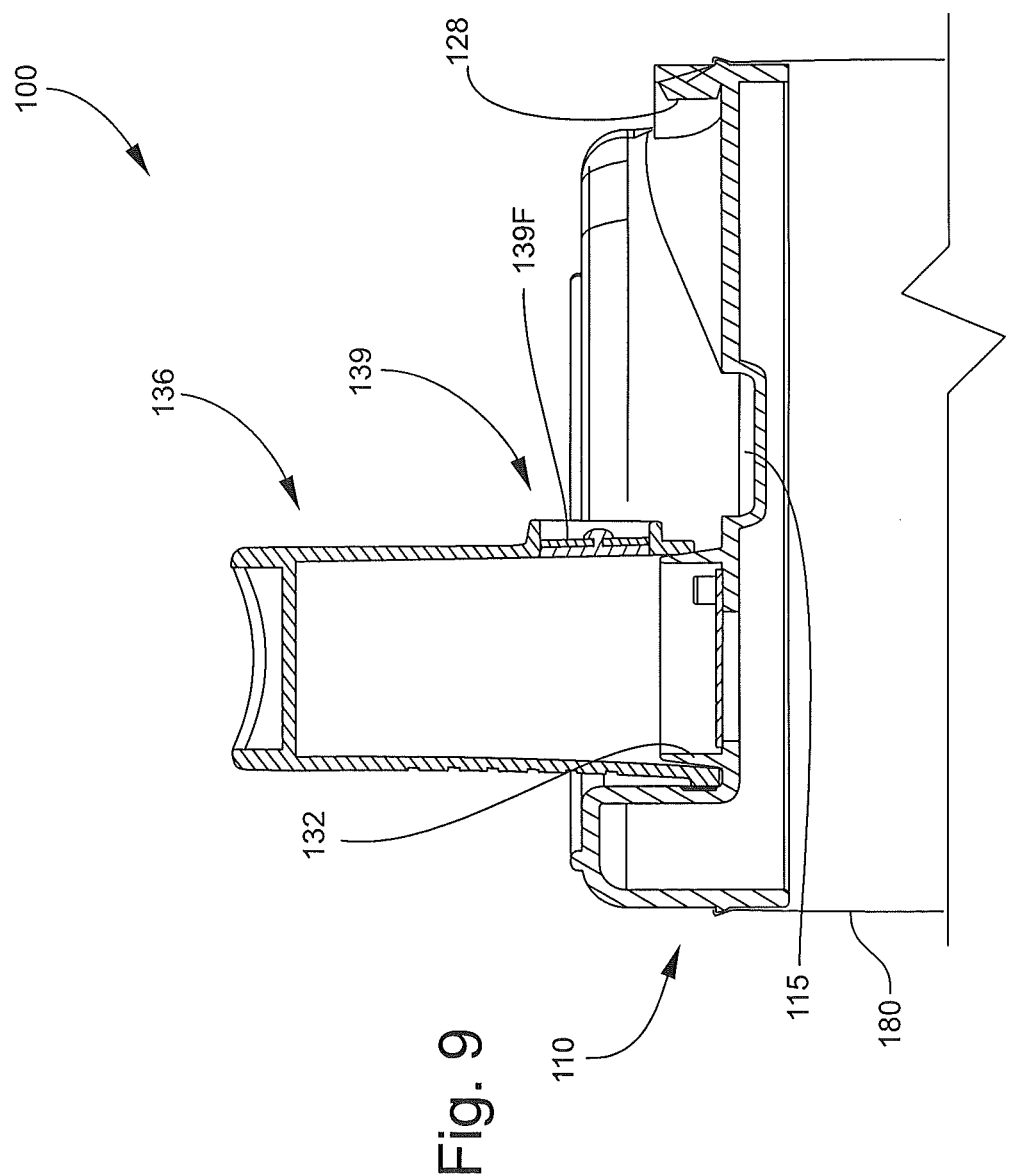

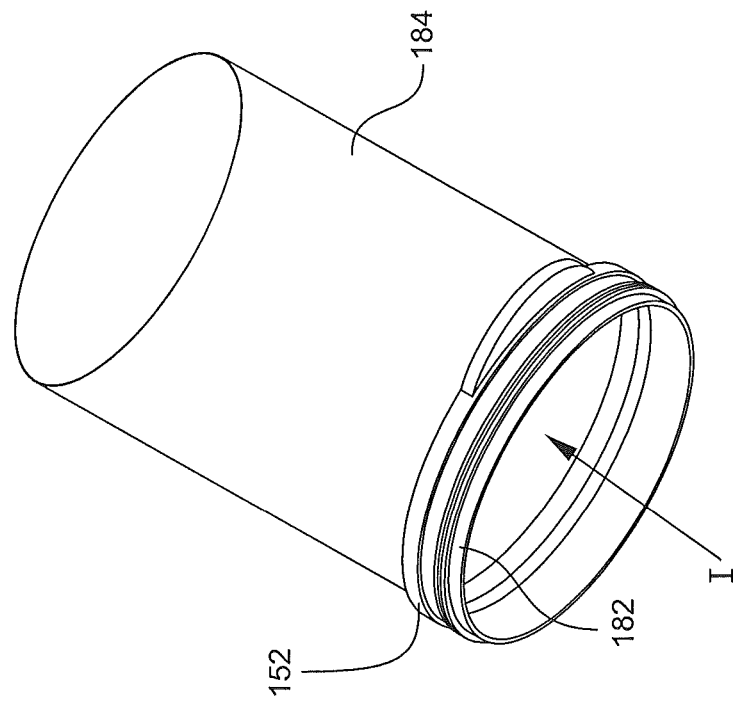
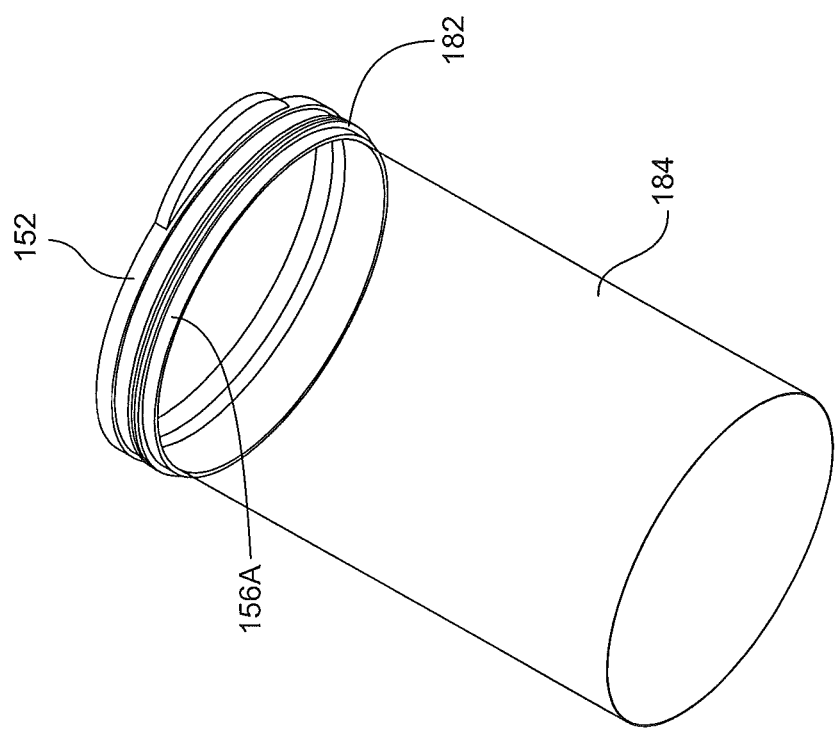
Fig. 11A
Fig. 11B

INHALATION DEVICES AND SYSTEMS AND METHODS INCLUDING THE SAME

RELATED APPLICATION(S)

This application is a continuation of U.S. patent application Ser. No. 13/862,533, filed Apr. 15, 2013, which claims the benefit of and priority from U.S. Provisional Patent Application No. 61/771,406, filed Mar. 1, 2013, and U.S. Provisional Patent Application No. 61/636,320, filed Apr. 20, 2012, the disclosures of which are incorporated herein by reference.

FIELD OF THE INVENTION

The present invention relates to inhalation devices and, more particularly, to inhalation devices and systems and methods including the same for delivering a dispersed dose of a medication for inhalation by a patient.

BACKGROUND OF THE INVENTION

Oronasal delivery of drugs has long been known and has gained wide acceptance. Pharmaceuticals for the treatment of tracheal, bronchial, nasal and pulmonary conditions are widely available in prescribed or metered doses in small pressurized aerosol canisters. While medications can be dispensed directly from such canisters into the oronasal passages of patients, experience has proven that patients generally have not made optimum use of and/or have not obtained optimum benefits from medications delivered directly from the aerosol canisters.

Because direct use of the aerosol canisters has not proven effective or efficient for a large proportion of patients, many devices have been proposed for converting the medications from the concentrated pressurized form in which they are discharged from aerosol canisters into a nonpressurized and less concentrated form in order to be more readily and efficaciously inhaled by the patient. Further, it has been found that a long and slow inspiration of the medication promotes a highly efficient distribution of medication to partially occluded airways. Thus, it is desirable in such devices to inhibit rapid inhalation and to encourage a long and slow inspiration period.

In order to promote a long and slow inspiration period, it is desirable to provide an expandable breathing bag or spacer, so that the patient is required during respiratory maneuvers to utilize a negative thoracic pressure upon inhalation, thereby to inhibit rapid inhalation and encourage long and slow inhalation. Representative prior art devices having expandable and contractible breathing bags or spacer chambers may be found by way of example, in U.S. Pat. No. 4,938,210 to Shene, U.S. Pat. No. 4,940,051 to Lankinen, U.S. Pat. No. 5,040,527 to Larson et al., U.S. Pat. No. 4,484,577 to Sackner et al., and U.S. Pat. No. 5,318,016 to Mecikalski.

SUMMARY OF THE INVENTION

According to embodiments of the present invention, a collapsible inhalation device for use with a metered dose inhaler (MDI) dispenser, the MDI dispenser operable to dispense a dose of a medication therefrom, includes an outlet end member, an inlet end member and a tubular, pliable, collapsible sleeve member. The outlet end member includes a mouthpiece. The inlet end member includes an inlet port and an MDI dispenser mount structure configured to receive and engage the MDI dispenser. The sleeve member has first and second opposed ends attached to the inlet end member and the outlet end member, respectively. The inhalation device is positionable in each of an open position, wherein the outlet end member and the inlet end member are spaced apart and the sleeve member is extended such that the outlet end member, the inlet end member and the sleeve member define a chamber, and a closed position, wherein the sleeve member is collapsed and the outlet end member and the inlet end member are proximate one another and envelope the sleeve member. When the inhalation device is in the open position with the MDI dispenser mounted in the MDI dispenser mount structure, a dose of the medication can be dispensed from the MDI dispenser into the chamber through the inlet port to mix with air in the chamber and thereby form a mixture of the air and the dose of the medication that can be inhaled by a patient from the chamber through the mouthpiece.

In some embodiments, the MDI dispenser includes an MDI aerosol canister mounted in an MDI holder having a dispensing section, and the inlet port and the MDI dispenser mount structure are configured to receive and engage the dispensing section such that the dispensing section extends through the inlet port.

The outlet end member may include a one-way inhalation valve that enables outflow of air from the chamber through the mouthpiece and prevents inflow of air into the chamber through the mouthpiece. In some embodiments, the mouthpiece further includes a one-way blowback relief valve that enables outflow of air from the mouthpiece through the one-way blowback relief valve and prevents inflow of air into the mouthpiece through the one-way blowback relief valve. The mouthpiece can include a trap structure configured to catch and prevent a component of the one-way inhalation valve from being inhaled through the mouthpiece.

In some embodiments, the sleeve member is substantially cylindrical when the inhalation device is in the open position.

The inhalation device can include a latch mechanism to releasably secure the outlet end member to the inlet end member when the inhalation device is in the closed position. The inhalation device can include at least one release tab operable by a user to actuate the latch mechanism to release the outlet end member from the inlet end member to open the inhalation device.

According to some embodiments, the inlet end member includes a ring member to which the sleeve member is affixed, and a cover member mounted on the ring member, wherein the cover member is removable from and replaceable on the ring member to provide access to the interior of the inhalation device for cleaning. In some embodiments, the cover member is formed of a first material including a resilient, deformable elastomer, and the ring member is formed of a second material more rigid than the first material.

According to some embodiments, the sleeve member is formed of a polymeric film having a thickness in the range of from about 4 to 8 mil. According to some embodiments, the polymeric film has a thickness in the range of from about 4 to 6 mil.

The sleeve member may be formed of a low density polyethylene (LDPE) film. In some embodiments, the LDPE film is an anti-static LDPE film having a surface resistivity of $1\times10^{12}$ Ohms/square or less as measured according to ASTM D257-07.

In some embodiments, at least a portion of at least one of the outlet end member and the inlet end member is formed of a polymeric material blended and/or coated with a supplemental material that imparts an anti-static property to the polymeric material.

According to some embodiments, one of the outlet end member and the inlet end member includes an annular ring member having a radially outwardly facing outer attachment surface and defining a through passage, wherein the sleeve member is bonded to the outer attachment surface and extends through the through passage to attach to the other of the outlet end member and the inlet end member. The sleeve member may be heat welded to the outer attachment surface.

According to some embodiments, the outlet end member includes a body and the mouthpiece is hingedly coupled to the body to rotate between an extended, deployed position and a retracted, stored position.

According to method embodiments of the present invention, a method for administering a dose of a medication to a patient from a metered dose inhaler (MDI) dispenser includes providing a collapsible inhalation device including: an outlet end member including a mouthpiece; an inlet end member including an inlet port and an MDI dispenser mount structure and configured to receive and engage the MDI dispenser; and a tubular, pliable, collapsible sleeve member having first and second opposed ends attached to the inlet end member and the outlet end member, respectively; wherein the inhalation device is positionable in each of an open position, wherein the outlet end member and the inlet end member are spaced apart and the sleeve member is extended such that the outlet end member, the inlet end member and the sleeve member define a chamber, and a closed position, wherein the sleeve member is collapsed and the outlet end member and the inlet end member are proximate one another and envelope the sleeve member. The method further includes: placing the inhalation device in the open position; mounting the MDI dispenser in the MDI dispenser mount structure; and thereafter dispensing a dose of the medication from the MDI dispenser into the chamber through the inlet port to mix with air in the chamber and thereby form a mixture of the air and the dose of the medication that can be inhaled by a patient from the chamber through the mouthpiece.

According to embodiments of the present invention, a collapsible inhalation device for use with a metered dose inhaler (MDI) dispenser, the MDI dispenser operable to dispense a dose of a medication therefrom, includes a rigid, unitary outlet end member, an inlet end member, and a tubular, pliable, collapsible sleeve member. The outlet end member includes a mouthpiece. The inlet end member includes an inlet port and an MDI dispenser mount structure configured to receive and engage the MDI dispenser. The sleeve member has first and second opposed ends attached to the inlet end member and the outlet end member, respectively, to define therewith a chamber. When the MDI dispenser is mounted in the MDI dispenser mount structure, a dose of the medication can be dispensed from the MDI dispenser into the chamber through the inlet port to mix with air in the chamber and thereby form a mixture of the air and the dose of the medication that can be inhaled by a patient from the chamber through the mouthpiece. The outlet end member further includes: a one-way inhalation valve that enables outflow of air from the chamber through the mouthpiece and prevents inflow of air into the chamber through the mouthpiece; and a one-way blowback relief valve that enables outflow of air from the mouthpiece through the one-way blowback relief valve and prevents inflow of air into the mouthpiece through the one-way blowback relief valve.

According to some embodiments, the sleeve member is formed of a polymeric film having a thickness in the range of from about 4 to 8 mil.

According to some embodiments, the outlet end member defines an exhaust port and at least one internal conduit fluidly connecting the mouthpiece to the exhaust port, and the outlet end member is configured to direct exhalation air flow from the patient through the mouthpiece, through the one-way blowback relief valve, through the at least one internal conduit, and out through the exhaust port. In some embodiments, the outlet end member includes a mouthpiece member, a backplate, and a valve member captured between the mouthpiece member and the backplate. The outlet end member and the backplate define an internal conduit in the outlet end member fluidly connecting the one-way blowback relief valve to the exhaust port. In some embodiments, the exhaust port is located on an axial end face of the outlet end member.

In some embodiments, the outlet end member includes a valve member including the one-way inhalation valve, and the one-way inhalation valve is a self-sealing valve. The one-way inhalation valve may be a duckbill valve. In some embodiments, the valve member further includes an integral, radially extending valve flap forming a part of the one-way blowback relief valve.

According to method embodiments of the present invention, a method for forming a collapsible inhalation device includes providing an end member including an annular ring member having a radially outwardly facing outer attachment surface and defining a through passage; providing a tubular, pliable, collapsible sleeve member having first and second sleeve sections; bonding the first sleeve section to the outer attachment surface; and routing the second sleeve section through the through passage.

In some embodiments, bonding the first sleeve section to the outer attachment surface includes heat welding the first sleeve section to the outer attachment surface.

The method may include inverting the sleeve member through itself and the through passage following the step of bonding the first sleeve section to the outer attachment surface.

Further features, advantages and details of the present invention will be appreciated by those of ordinary skill in the art from a reading of the figures and the detailed description of the embodiments that follow, such description being merely illustrative of the present invention.

BRIEF DESCRIPTION OF THE DRAWINGS

FIG. 9 is an enlarged, fragmentary, cross-sectional view of the inhalation device of FIG. 2 with the mouthpiece in the extended, deployed position.

FIGS. 11A and 11B illustrate methods for constructing the inhalation device of FIG. 2.

DETAILED DESCRIPTION OF EMBODIMENTS OF THE INVENTION

Figure 1:
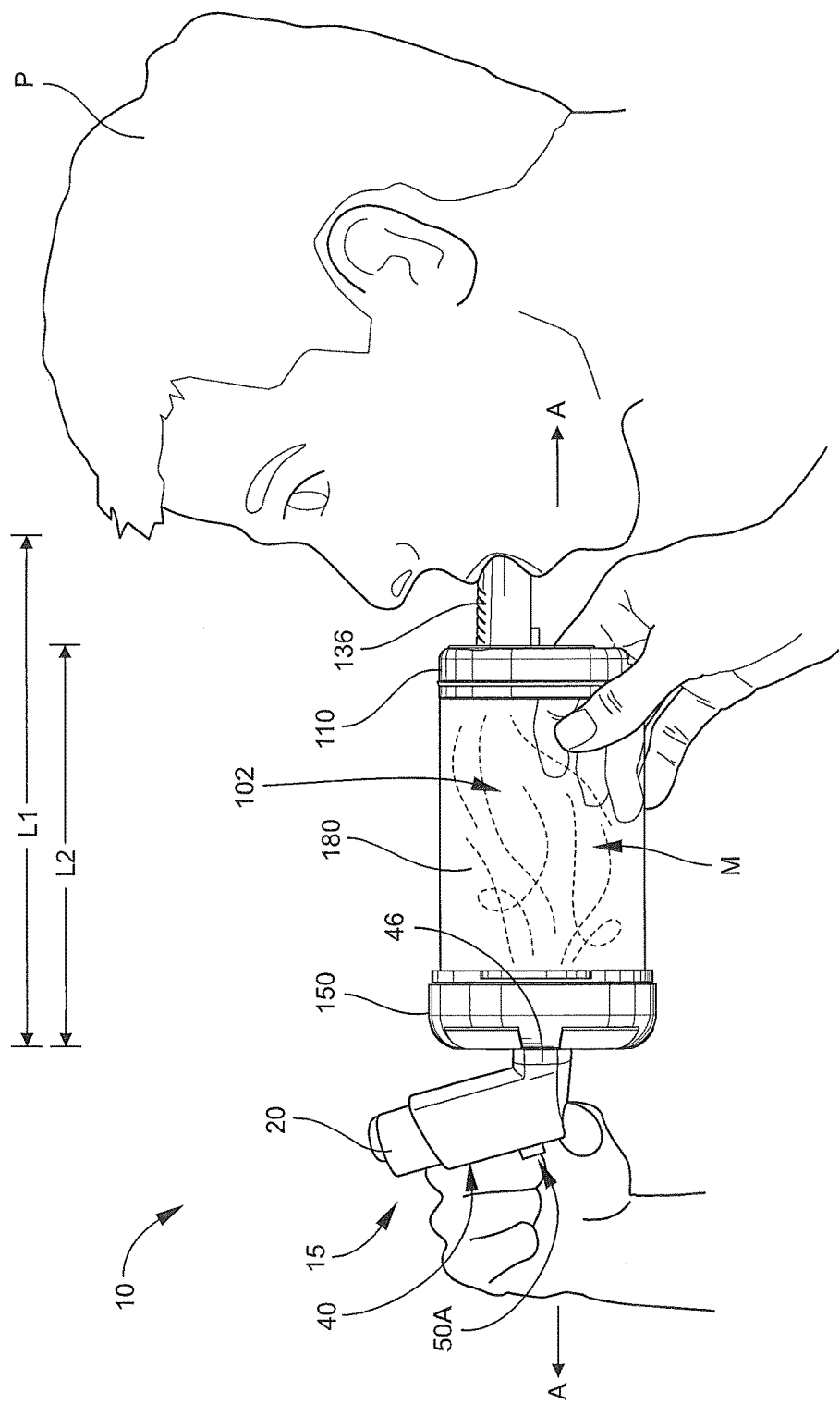
FIG. 1 is side elevational view of an inhalation system according to embodiments of the present invention being used by a patient to administer a dose of an inhalable medication.

The present invention now will be described more fully hereinafter with reference to the accompanying drawings, in which illustrative embodiments of the invention are shown. In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that when an element is referred to as being "coupled" or "connected" to another element, it can be directly coupled or connected to the other element or intervening elements may also be present. In contrast, when an element is referred to as being "directly coupled" or "directly connected" to another element, there are no intervening elements present. Like numbers refer to like elements throughout.

In addition, spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the expression "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, "monolithic" means an object that is a single, unitary piece formed or composed of a material without joints or seams.

Embodiments of the present invention can provide inhalation devices or so-called spacers for administering oral nasal medications. The inhalation devices can convert medications for treatment of tracheal, bronchial, nasal and pulmonary conditions from a concentrated pressurized aerosol form into a nonpressurized, air diluted form for ease and greater efficacy of inhalation by a patient suffering from such a condition.

Figure 12:
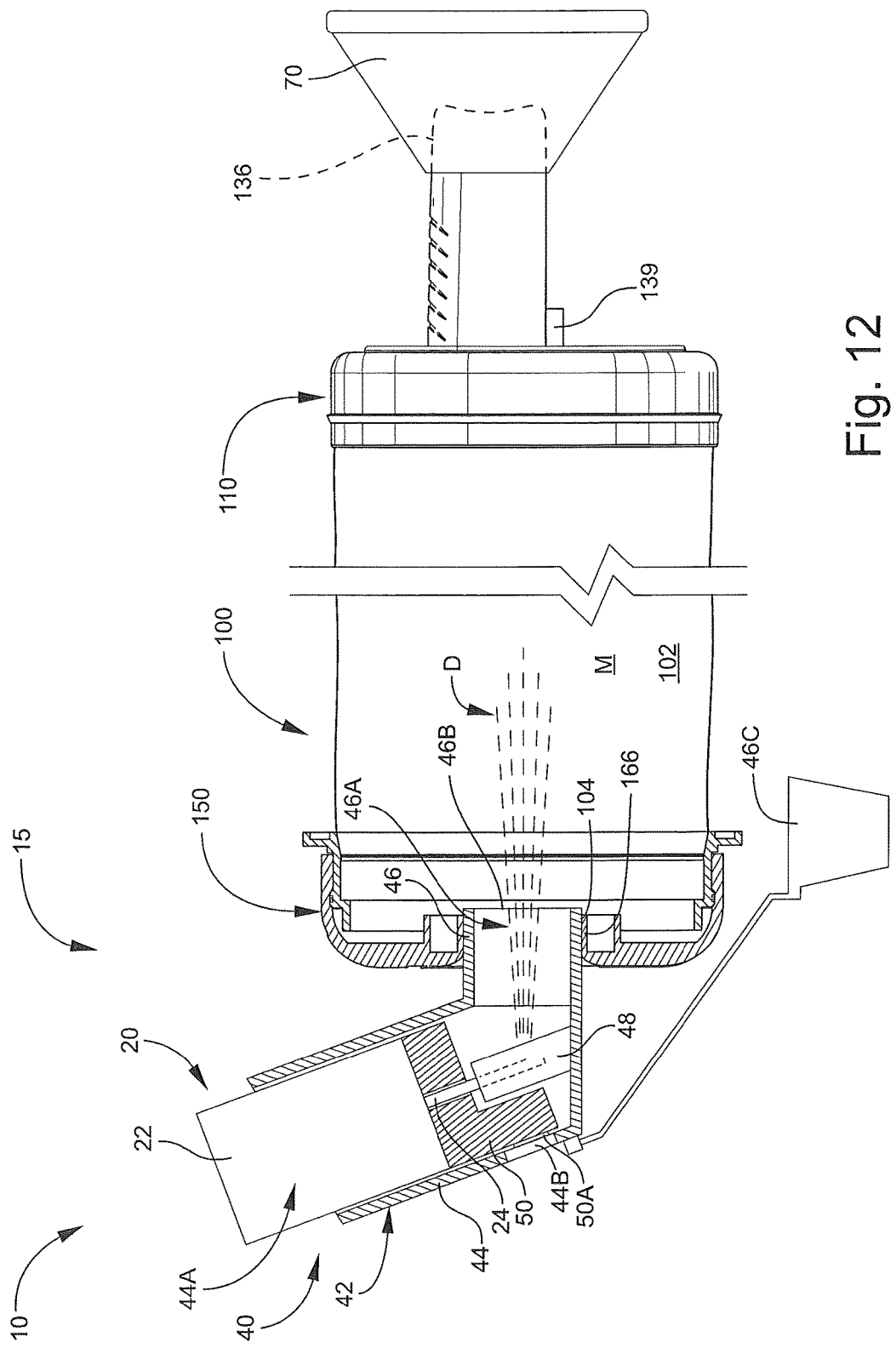
FIG. 12 is an enlarged, fragmentary, cross-sectional view of the inhalation system of FIG. 1.
Figure 13:
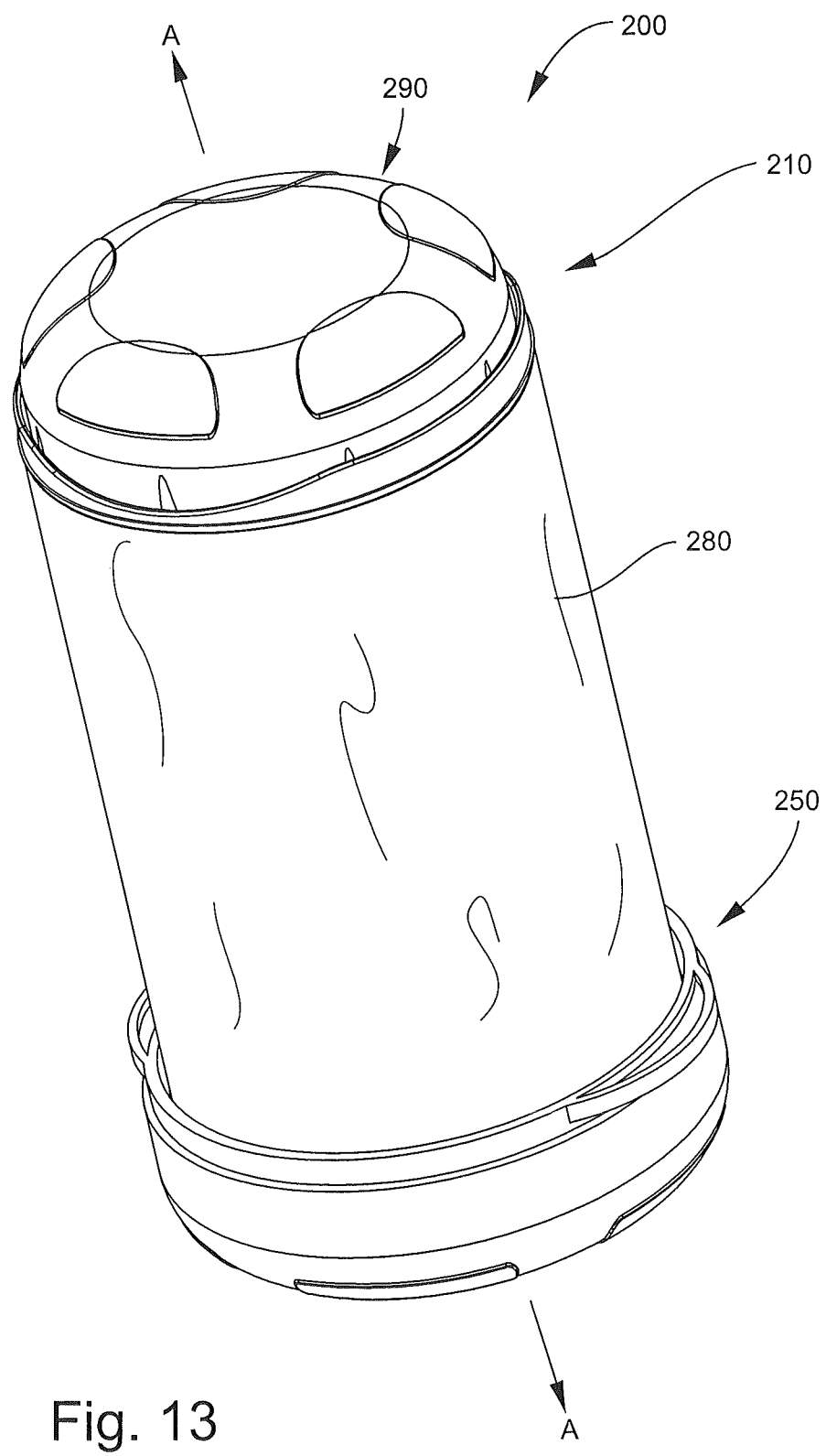
FIG. 13 is a front, top perspective view of a collapsible inhalation device according to further embodiments of the present invention.
Figure 14:
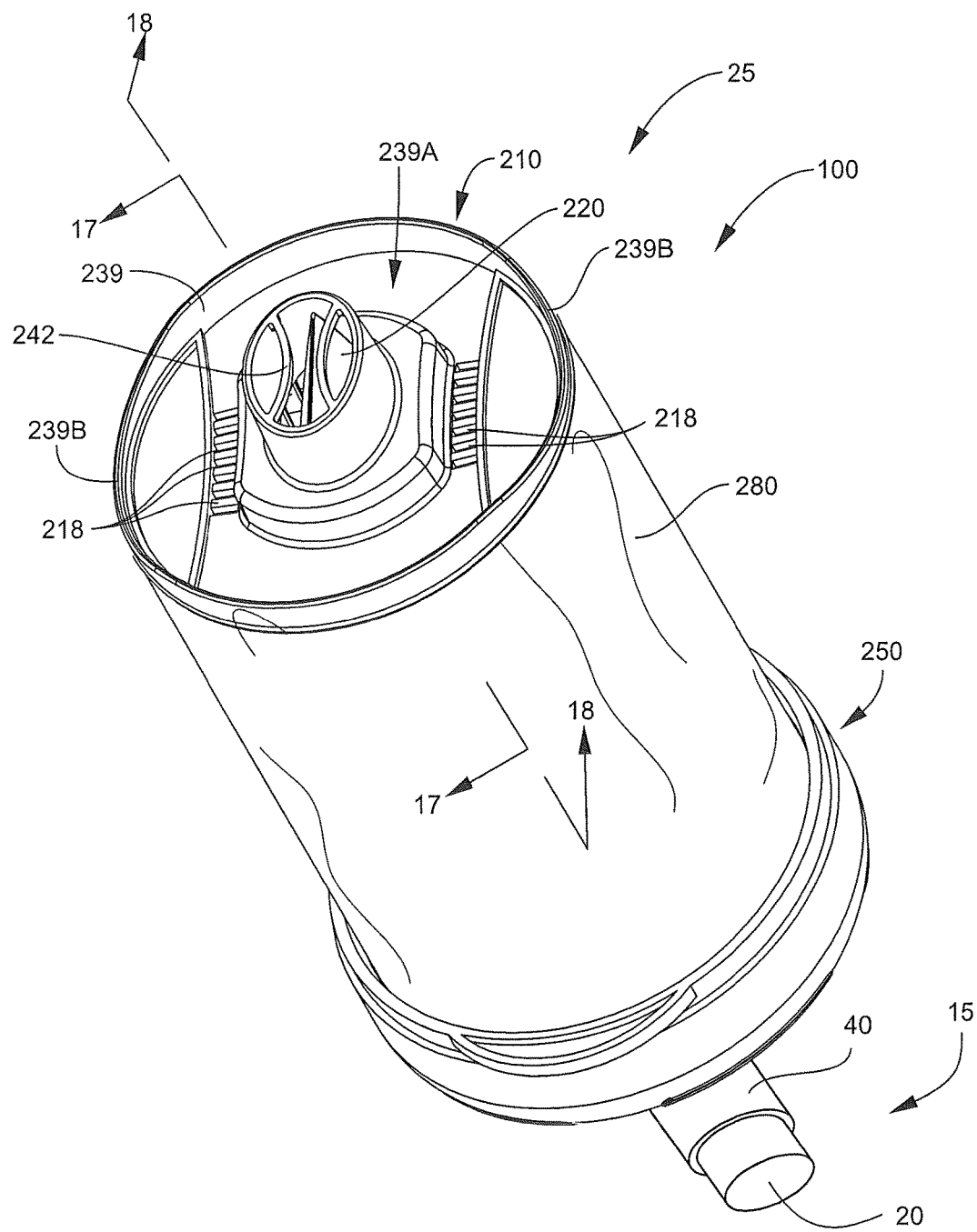
FIG. 14 is a front, top perspective view of an inhalation system including the inhalation device of FIG. 13.
Figure 15:
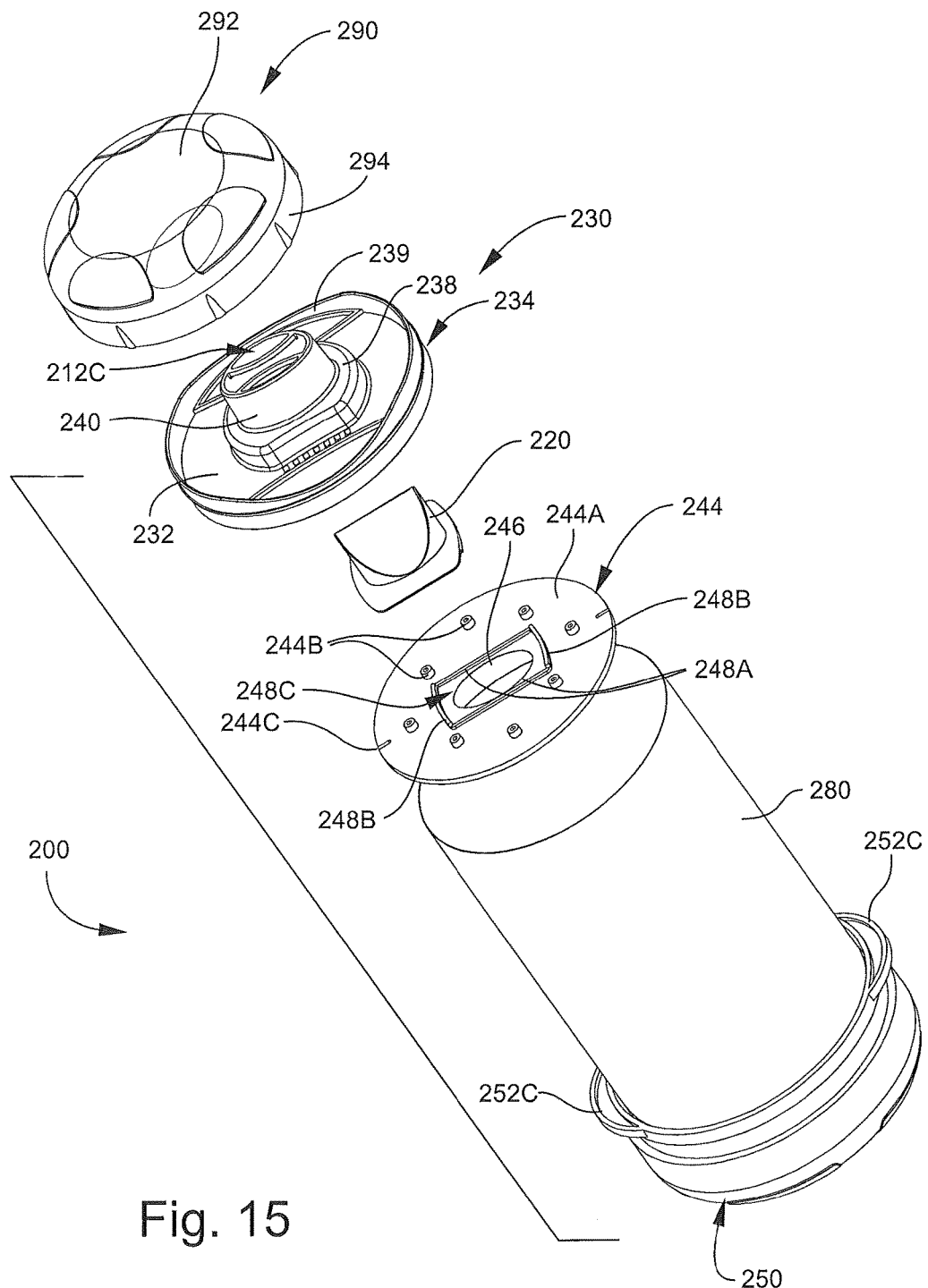
FIG. 15 is an exploded, front, top perspective view of the inhalation device of FIG. 13.

With reference to FIGS. 1-12, an inhalation device or spacer 100 according to embodiments of the present invention is shown therein. The inhalation device 100 may be used in conjunction with an inhalable medication dispenser 15 (FIGS. 1 and 12), for example, to form an inhalation system 10 to deliver medication from the dispenser 15 in an air diluted and nonpressurized form to the oronasal breathing passages of a human patient P. According to some embodiments and as illustrated in FIG. 12, the dispenser 15 can be actuated to inject a prescribed or predetermined metered dose D of the medication into a chamber 102 defined by the inhalation device 100, where the medication dose is mixed with air in the chamber 102 to form a dispersed, gaseous medicine mixture M. A patient P can then inhale the mixture M from the inhalation device 100 through a mouthpiece 136 of the inhalation device 100.

The inhalation device 100 can be adapted or configured to effectively receive and engage inhalable medication dispensers of a variety of form factors including conventional dispensers comprising a metered dose inhaler (MDI) aerosol canister mounted in an L-shaped holder of the type commonly referred to as a boot. As a result, the inhalation device 100 can enable the user to effectively use features and benefits attendant to the dispenser itself. In particular, according to some embodiments, the dispenser 15 includes an integral dose counter 50 (FIG. 12) that maintains a running count of the number of doses D that have been dispensed therefrom.

Figure 10A:
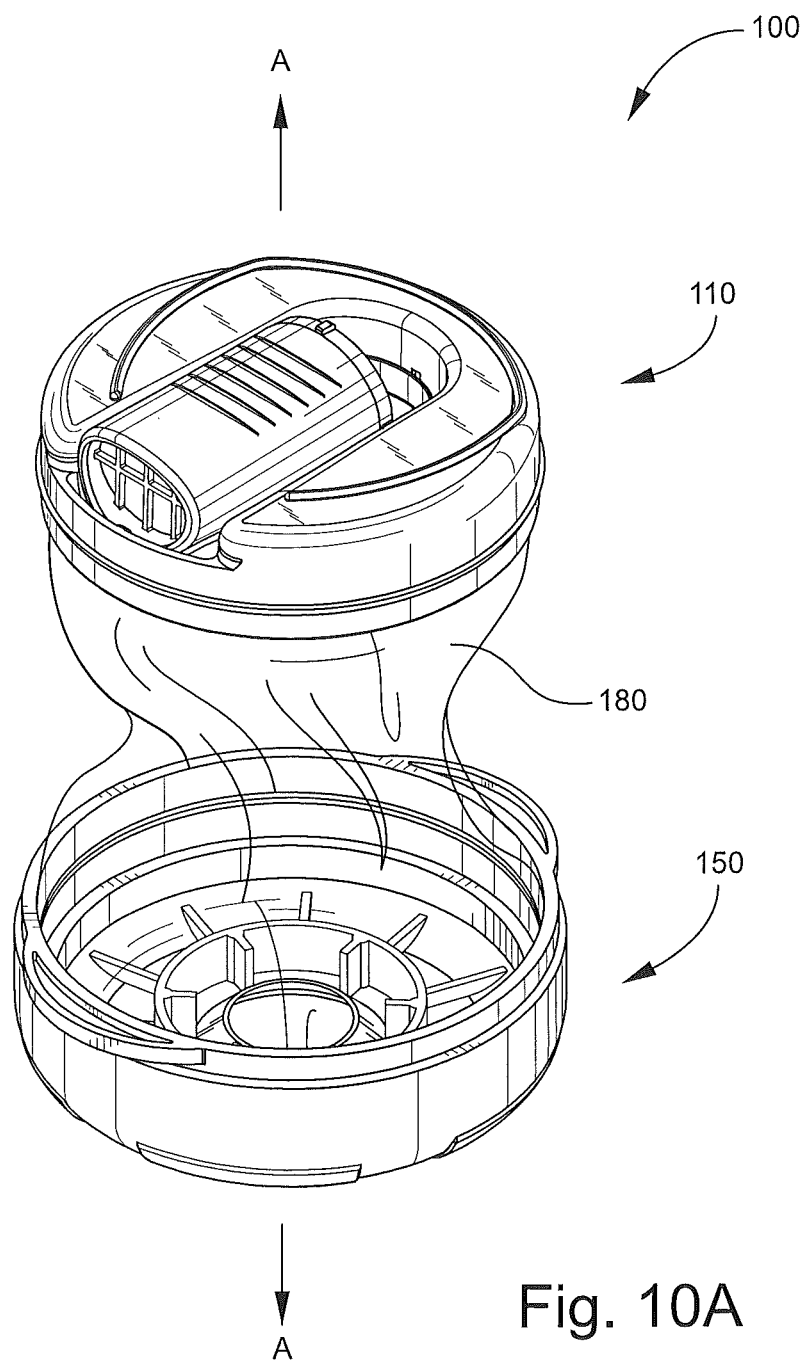
FIG. 10A is a top perspective view of the inhalation device of FIG. 2 in a partially collapsed position.
Figure 10B:
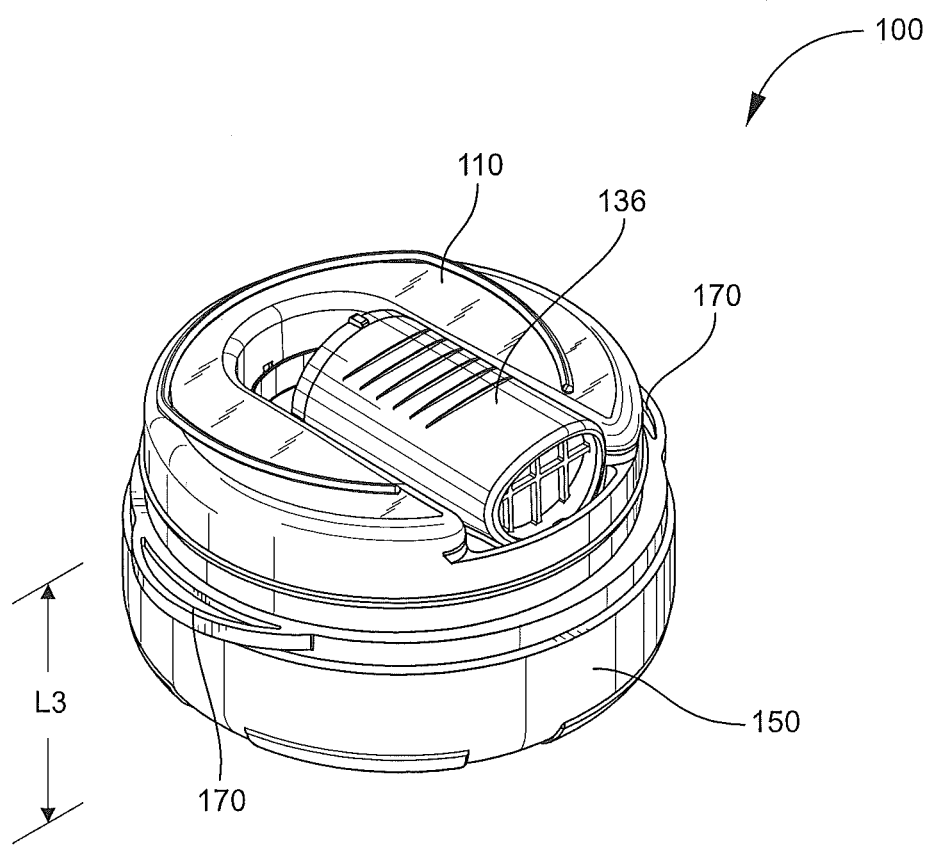
FIG. 10B is a front, top perspective view of the inhalation device of FIG. 2 in a closed position.

Advantageously, the inhalation device 100 can be collapsed into a relatively compact form factor when not in use, as shown in FIG. 10B. Further advantages and aspects of inhalation devices and spacers according to embodiments of the present invention will be apparent from the description that follows.

The medicine dispensed from the dispenser 15 may be any suitable medicine for oronasal delivery. According to some embodiments, the medicine is delivered as a fine powder. According to some embodiments, the medicine is delivered as fine liquid droplets.

As discussed above and with reference to FIG. 12, the dispenser 15 may include a metered dose inhaler (MDI) unit 20 and a holder or boot 40. The MDI unit 20 may be of any suitable construction, including MDI units of conventional and well-known designs. According to some embodiments, the MDI unit 20 includes an aerosol canister 22 and a dispensing nozzle 24. As is well-known, the contents of the canister 22 (i.e., the medication) are under pressure substantially greater than ambient and can be dispensed by depressing the nozzle 24. Typically, the actuator of the MDI unit 20 is configured so that with each depression, the nozzle 24 will cause the MDI unit 20 to dispense or eject a metered, predetermined amount of the medication (i.e., the predetermined dose). Suitable MDI units may include ProAir® HFA (albuterol sulfate), Symbicort® (budesonide/formoterol fumarate dihydrate; includes counter), Advair® HFA (fluticasone propionate and salmeterol; includes counter), and Proventil® HFA (albuterol sulfate).

The MDI unit holder 40 may be of any suitable construction, including holders or boots of conventional and well-known designs. According to some embodiments, the boot 40 includes a body 42 having a canister section 44 and a dispensing section 46. The canister section 44 defines a cavity 44A to hold the canister 22. The dispensing section 46 defines a dispensing passage 46A terminating at an exit opening 46B. An actuator, which may be integrally molded with the sections 44, 46, is provided between the cavity 44A and the passage 46A. The counter device 50 has a display 50A and is also mounted in the body 42. The body 42 includes a window opening 44B to enable a user to view the display 50A. A protective end cap 46C may be provided to selectively fit over and seal the opening 46B. Suitable holders may include those provided with ProAir® HFA (albuterol sulfate), Symbicort® (budesonide/formoterol fumarate dihydrate; includes counter), Advair® HFA (fluticasone propionate and salmeterol; includes counter), and Proventil® HFA (albuterol sulfate). The counter device 50 may include a transducer that generates a signal responsive to a predetermined pressure change or level (i.e., corresponding to an actuation of the MDI unit 20), and a controller (e.g., an integrated circuit) that processes the signal and generates a count display on the display 50A. Other suitable counters may be fully or partially mechanical counters.

With reference to FIGS. 2-7, the inhalation device 100 has a longitudinal axis A-A (FIG. 1) and includes an outlet end member 110 (hereinafter, the head 110), an inlet end member 150 (hereinafter, the base 150), and a pliable, flexible bag or sleeve member 180. The head 110, the base 150, and the sleeve member 180 collectively define the chamber 102. The base 150 includes an inlet opening or aerosol injection port 104 communicating with the chamber 102. The mouthpiece 136 forms a part of the head 110 and defines an outlet opening 136B (FIG. 7) selectively communicating with the chamber 102 when the mouthpiece 136 is deployed.

Figure 2:
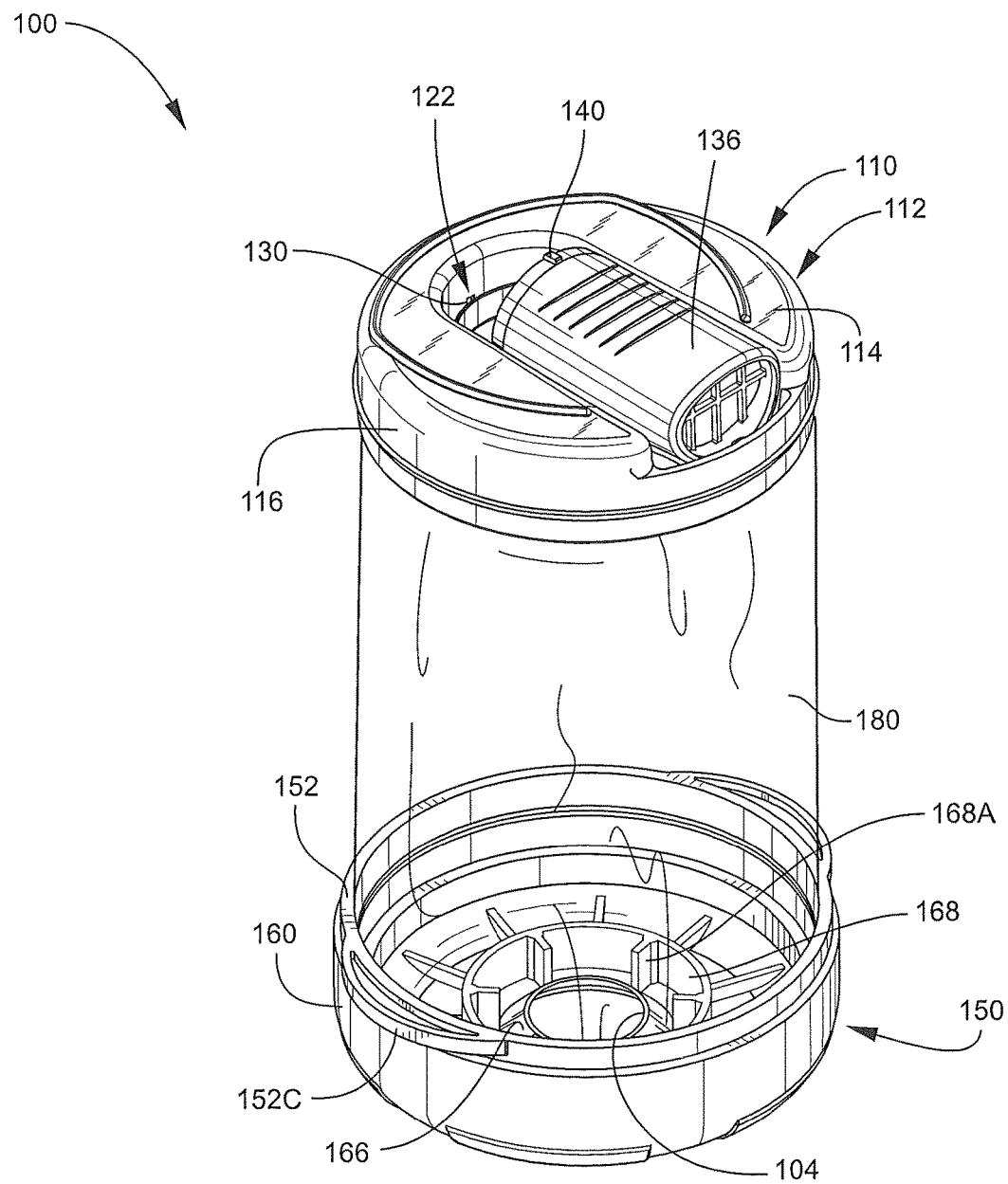
FIG. 2 is a front, top perspective view of a collapsible inhalation device according to embodiments of the present invention and forming a part of the inhalation system of FIG. 1.
Figure 6:
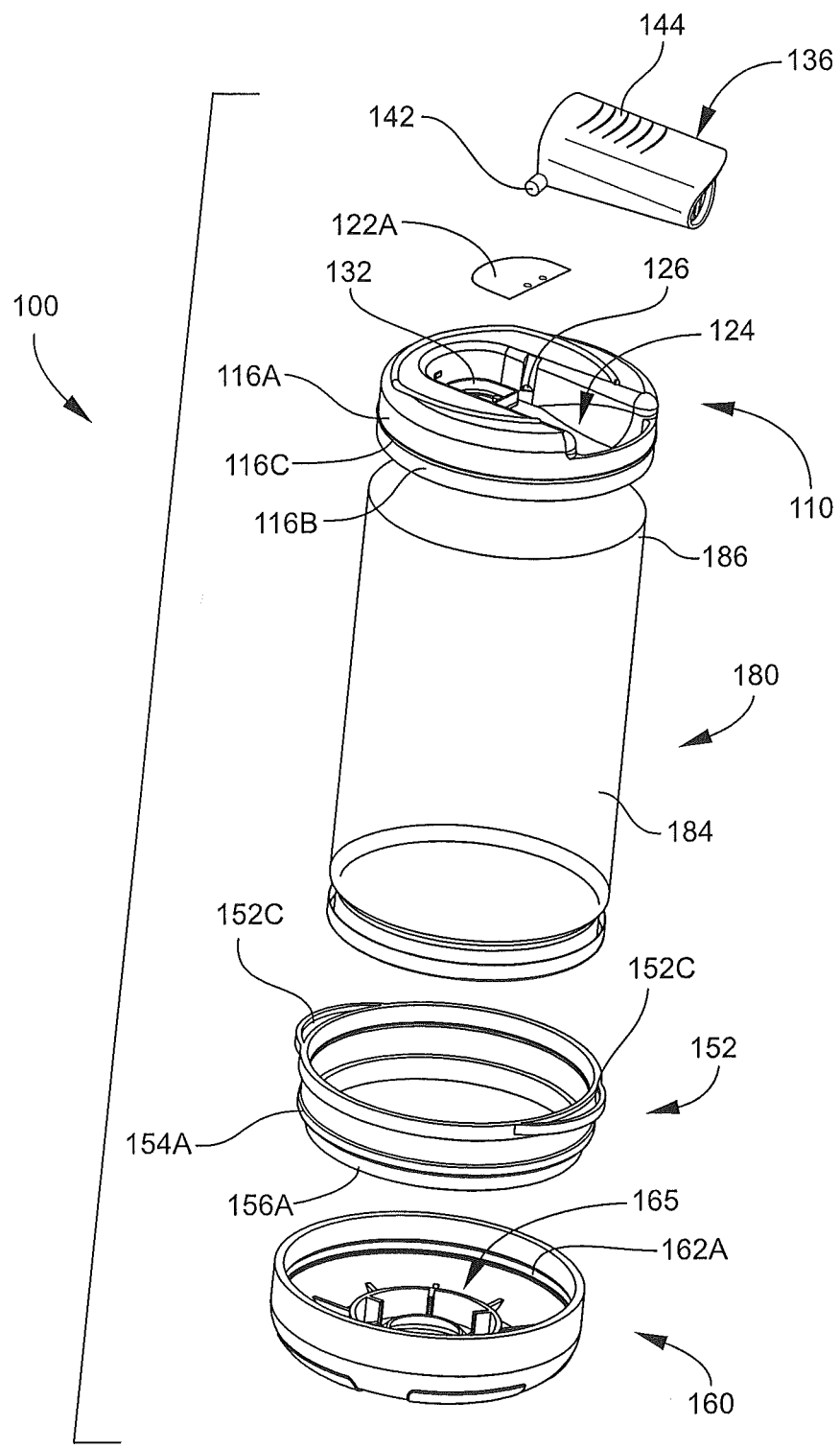
FIG. 6 is an exploded, front, top perspective view of the inhalation device of FIG. 2.

Turning to the head 110 in more detail, the head 110 includes a body 112 (FIG. 2). The body 112 has an end wall 114 and an integral sidewall 116. An opening 120 (FIGS. 3 and 7) is defined in the end wall 114 for outflow of air or mixture M from the chamber 102. As shown in FIG. 6, the sidewall 116 includes an annular upper sidewall section 116A contiguous with the end wall 114, an annular attachment flange 116B depending from the upper sidewall section 116A, and an annular bead or rib 116C extending along the interface between the section 116A and the flange 116B. An upstanding, annular guide wall 132 (FIG. 6) surrounds the opening 120.

Figure 3:
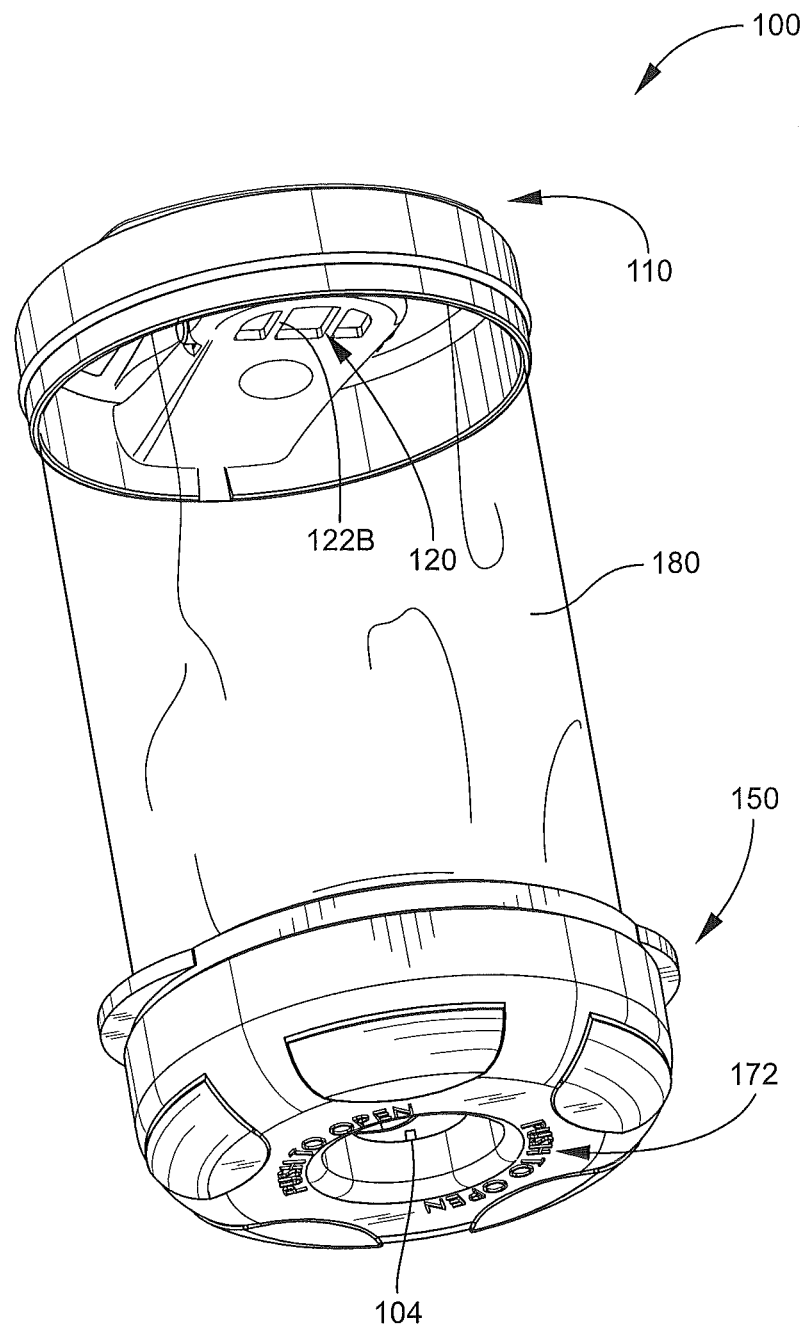
FIG. 3 is a bottom, rear perspective view of the inhalation device of FIG. 2.
Figure 4:
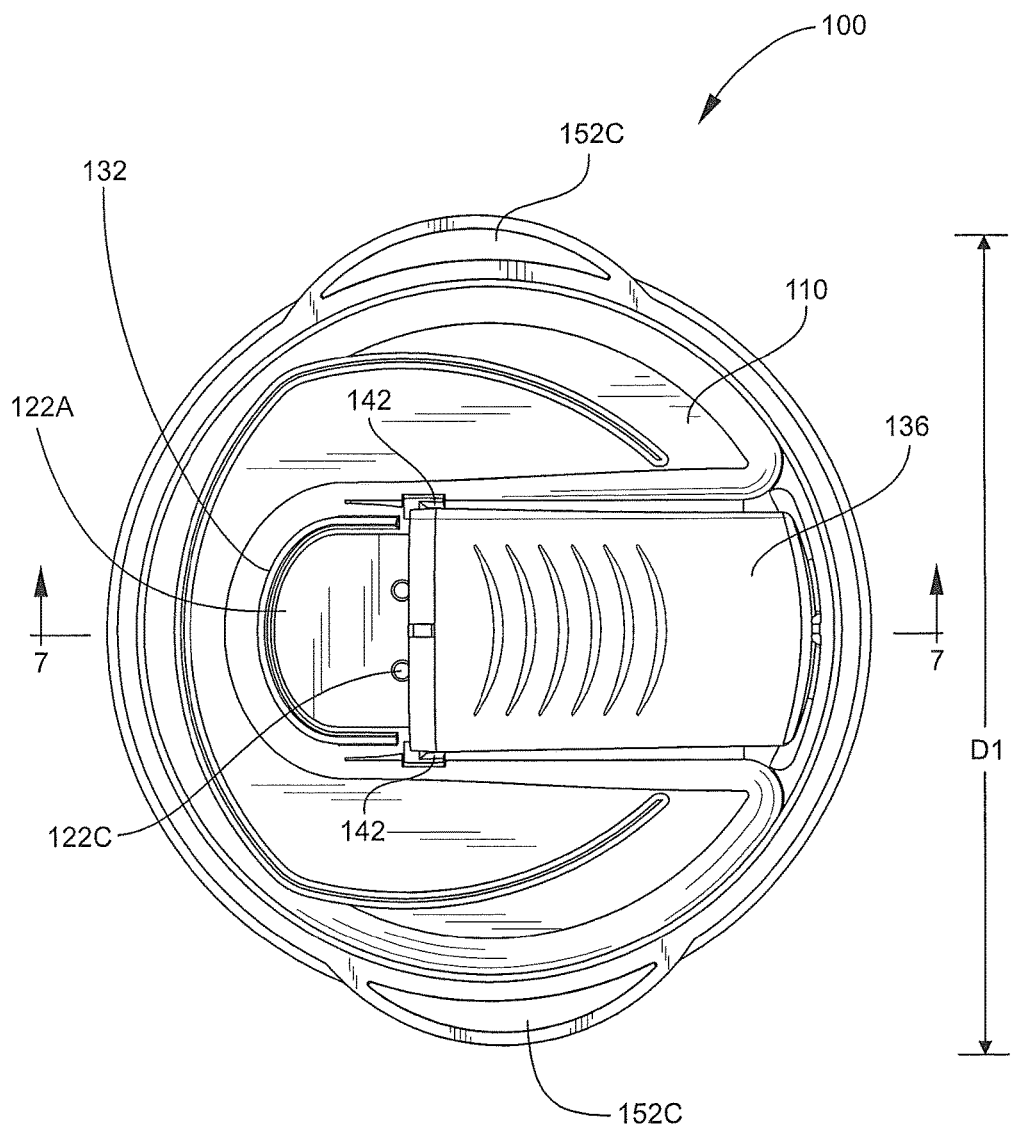
FIG. 4 is a top plan view of the inhalation device of FIG. 2.
Figure 5:
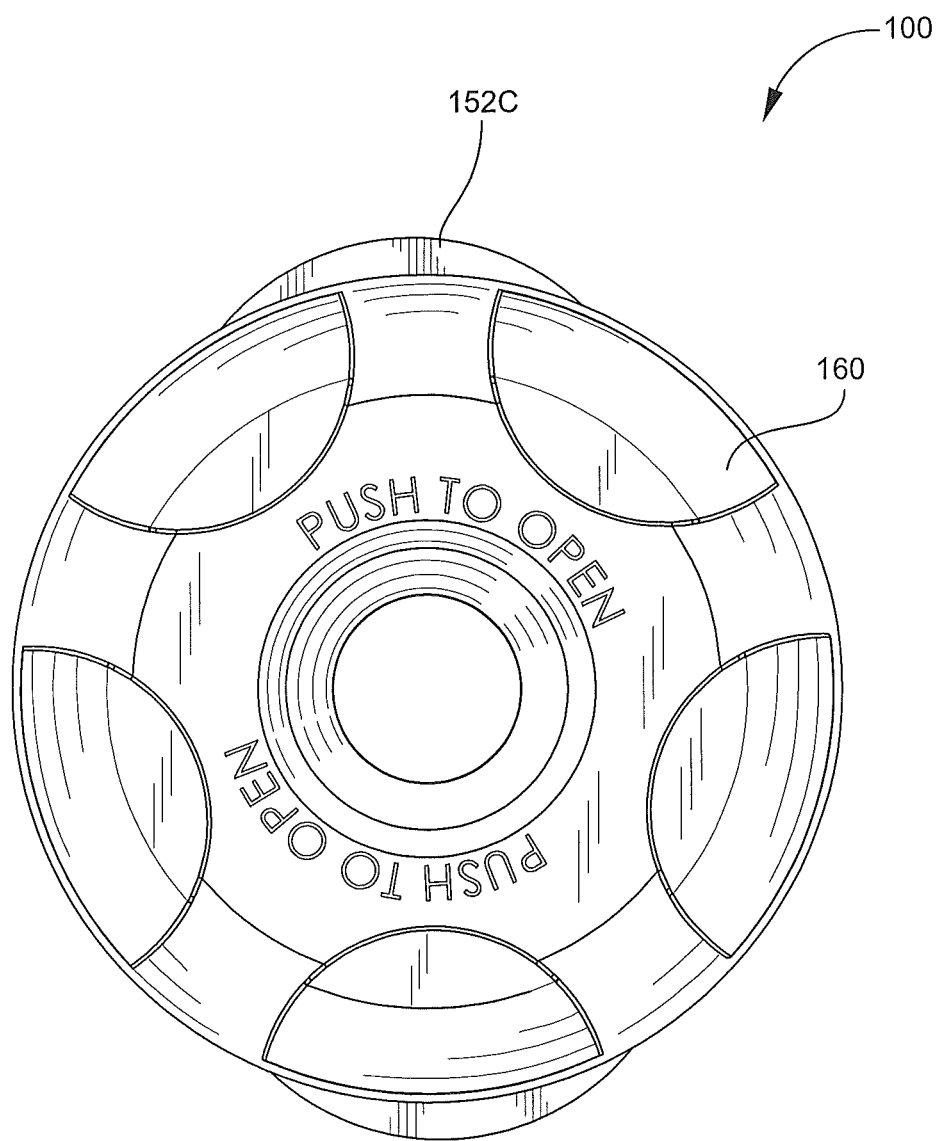
FIG. 5 is a bottom plan view of the inhalation device of FIG. 2.

A one-way inhalation valve 122 (FIG. 7) is located across the opening 120 and configured to permit the air or mixture M to flow out of the chamber 102 through the opening 120 while preventing air, debris or the like from being displaced, forced or drawn into the chamber 102 through the opening 120. The valve 122 can also prevent or inhibit air and medication from escaping the chamber 102 prior to inhalation. More particularly, the valve 122 includes a valve member, diaphragm or flap 122A (FIGS. 4 and 6) secured to the end wall 114 by anchors 122C (e.g., heat stakes; FIG. 6) and limited by stop bars 122B (FIG. 3).

The mouthpiece 136 defines a through passage 137 (FIG. 7) terminating at an inlet opening 136A and an opposed outlet opening 136B. A trap structure, filter or grill 138 may be provided in the passage (e.g., at or proximate the outlet opening 136B). The trap structure 138 may serve to inhibit or prevent the entry of foreign objects or debris into the mouthpiece 136 as well as to ensure that the valve flap 122A, if it were to become detached from the end wall 114, is not inhale by the patient. Grip grooves 144 (FIG. 6) or the like may be provided to facilitate manipulation of the mouthpiece 136.

Figure 7:
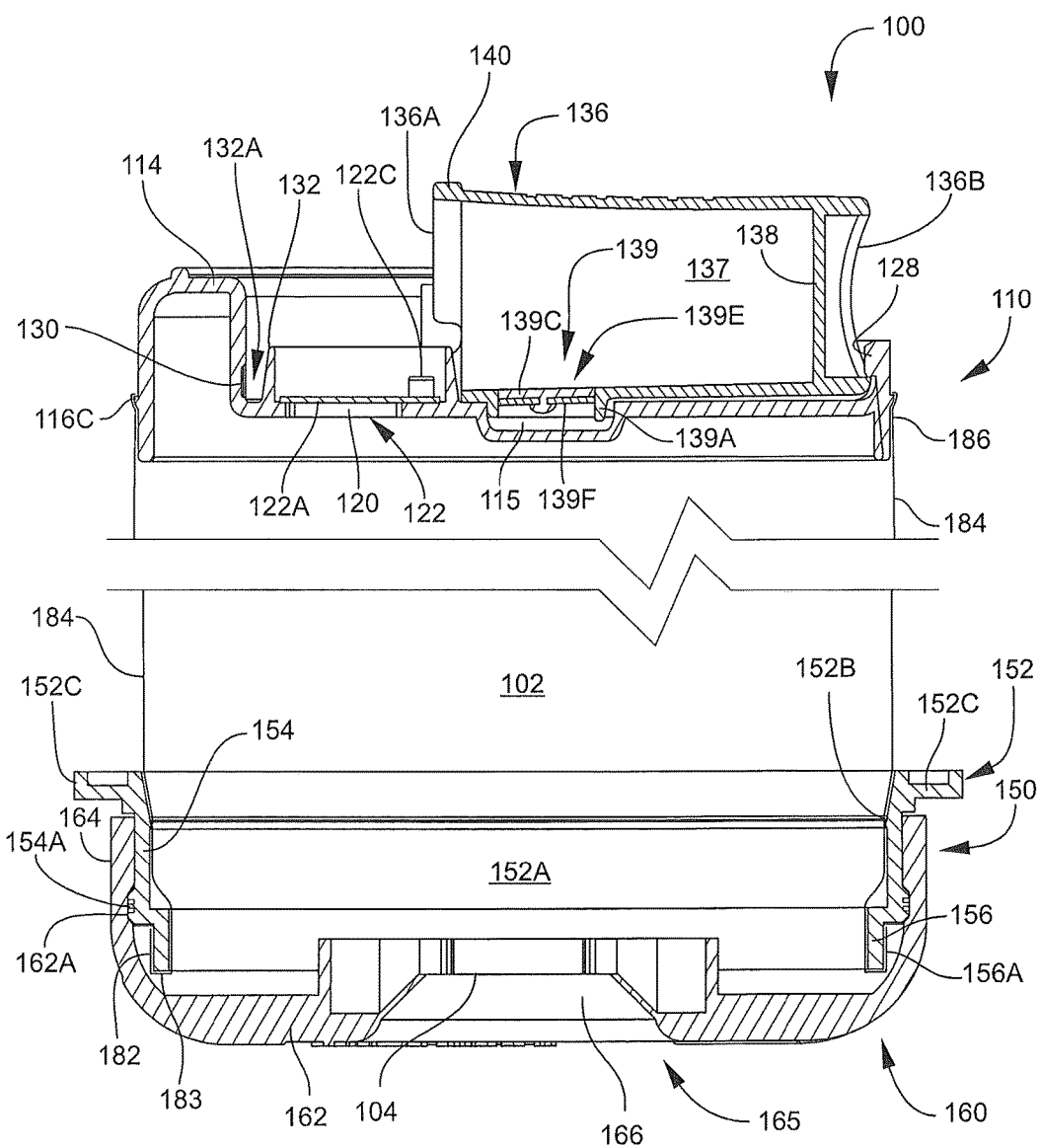
FIG. 7 is a fragmentary, cross-sectional view of the inhalation device of FIG. 2 taken along the line 7-7 of FIG. 4.
Figure 8:
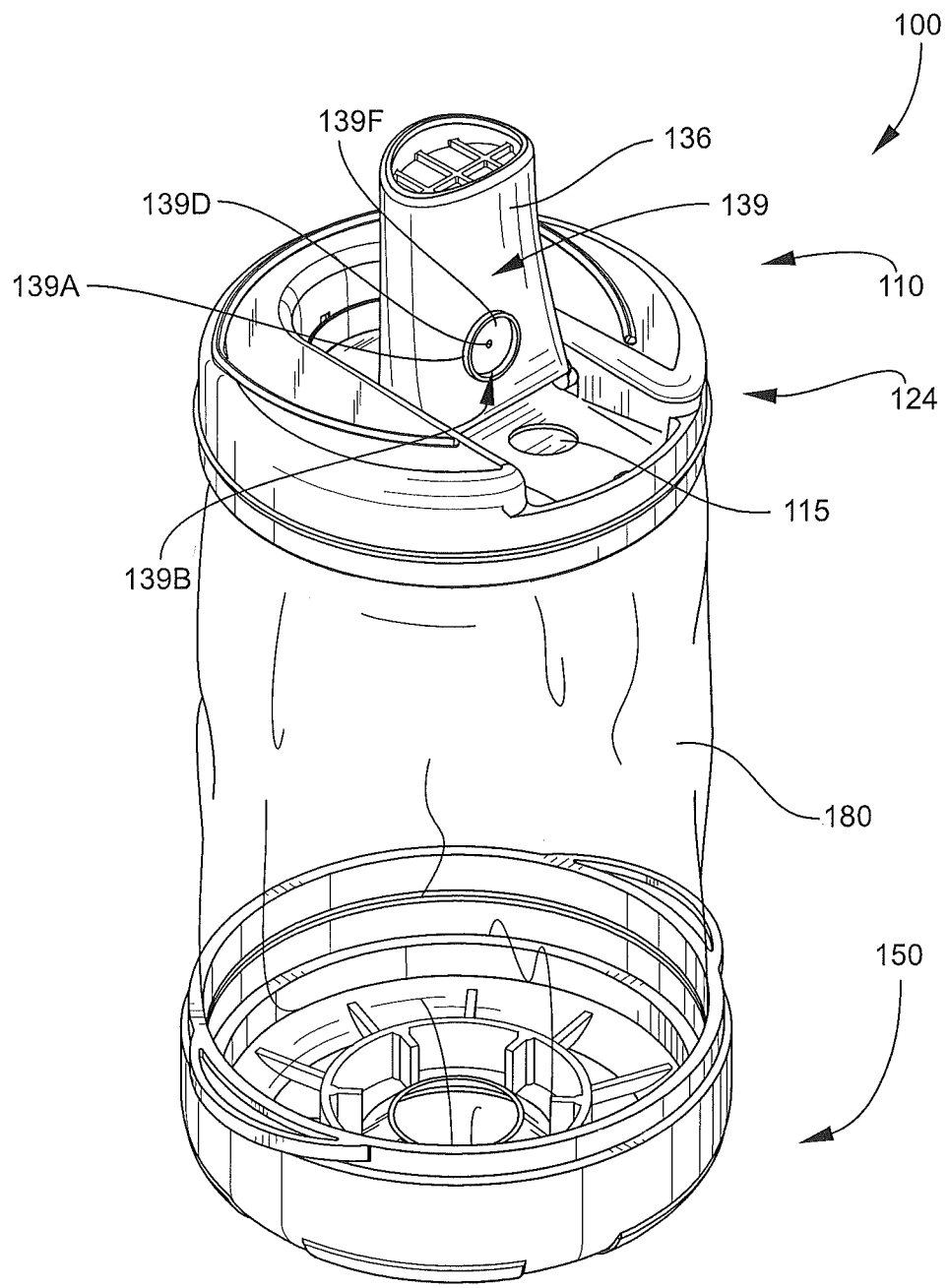
FIG. 8 is a front, top perspective view of the inhalation device of FIG. 2 with a mouthpiece thereof in an extended, deployed position.

The mouthpiece 136 is foldable about the hinge between a stored position as shown in FIG. 2 and an operative or deployed position as shown in FIGS. 1, 8 and 9. The end wall 114 defines a mouthpiece recess 124 (FIG. 8) within which the mouthpiece 136 resides when in the stored position to provide a low profile. The mouthpiece 136 is pivotally coupled to the end wall 114 by hinge projections 142 that rotatably seat in holes or detents 126 (FIG. 6). Latch features may be provided to releasably secure the mouthpiece 136 in the stored and/or the deployed position. For example, a front latch tab 128 is provided to releasably engage the front end of the mouthpiece 136 to hold the mouthpiece 136 in the stored position as shown in FIG. 7. A rear latch tab 140 on the mouthpiece 136 is provided to releasably engage a latch feature in the form of a detent 130 on the end wall 114 when the mouthpiece 136 is in the extended position of FIG. 9.

The mouthpiece 136 may also be provided with a one-way exhalation or blowback relief valve 139 (FIGS. 7 and 8). The valve 139 includes an upstanding annular wall 139A on the lower side of the mouthpiece 136. The wall 139A defines a cavity 139B communicating with a valve opening 139E extending through the mouthpiece 136. Stop bars 139C extend across the opening 136E and support a mounting post 139D. A valve member, diaphragm or flap 139F is mounted on and affixed to (e.g., by heat staking) the post 139D on the outer side of the stop bars 139C. The flap 139F is recessed to prevent removal. The valve 139 is thus configured to permit flow of pressurized air out of the mouthpiece 136 through the opening 139E while preventing inflow through the opening 139E. A recess 115 is provided in the end wall 114 to receive all or a portion of the valve 139 when the mouthpiece 136 is in the retracted position.

Turning to the base 150 in more detail, the base 150 includes an annular ring member 152 and a cover member 160. The cover member 160 may be detachably and re-attachably secured to the ring member 152.

Referring to FIG. 7, the ring member 152 includes an annular upper section 154 and an annular attachment flange 156 that collectively define an inner passage 152A. An annular outer coupling rib 154A extends radially outwardly from the upper section 154. The attachment flange 156 has an outer surface 156A. The ring member 152 further includes one or more annular latch grooves 152B defined in the inner diameter surface thereof and opposed release tabs 152C (FIG. 4) extending radially outwardly at or proximate the top edge of the ring member 152.

The cover member 160 (FIG. 7) includes an end wall 162 and an annular sidewall 164 depending therefrom. An annular inner coupling groove 164A is defined in the sidewall 164 and positioned and configured to mate with the coupling rib 154A. The cover member 160 includes a dispenser mount structure 165 including a deformable, resilient sealing flange 166 extending axially inwardly from the end wall 162. The inner, distal edge of the sealing flange 166 defines the inlet opening 104. The sealing flange 166 and the inlet opening 104 are sized and shaped to receive and hold the dispensing section 46 of the holder 40. According to some embodiments, the mount structure 165 is configured such that the section 46 can be inserted into the inlet opening 104 without requiring undue force but, once installed, will resist inadvertent or non-deliberate forces tending to withdraw the holder 40 from the cover member 160. According to some embodiments and as shown, the sealing flange 166 is frusto-conical and tapers radially inwardly as the sealing flange 166 extends further into the chamber 102. A reinforcement wall 168 (FIG. 2) and ribs 168A may be provided to reinforce the end wall 162 and the sealing flange 166. The cover member 160 further includes indicia 172 (FIG. 3). According to some embodiments, the cover member 160, when mounted on the ring member 152, provides a substantially airtight seal therebetween (FIG. 2).

The sleeve member 180 is continuous, tubular and open at either end. The sleeve member 180 is formed of a flexible, pliable, collapsible film or layer and, according to some embodiments, a polymeric film layer. With reference to FIG. 7, the sleeve member 180 includes a base attachment section 182, a transitional section 183, a main section 184, and a head attachment section 186. The base attachment section 182 is attached to the ring member 152 and the head attachment section 186 is attached to the head body 112 as discussed in more detail below. The transitional section 183 provides a transition between the base attachment section 182 and the main section 184. The main section 184 defines, in part, the chamber 102. According to some embodiments, when the device 100 is in the open position, the sleeve member 180 is substantially cylindrical.

According to some embodiments and with reference to FIGS. 7, 11A and 11B, the sleeve member 180 is secured to the base 150 using the following inventive method. The base attachment section 182 is placed around and bonded to the outer surface 156A of the attachment flange 156 of the ring member 152. The outer coupling rib 154A can be used to locate the terminal edge of the sleeve member 180. According to some embodiments, the section 182 is heat welded to the surface 156A. The sleeve member 180 is then inverted through itself and the inner passage 152A of the ring member 152 as shown in FIG. 11B such that the transitional section 183 wraps around the ring member 152.

The head attachment section 186 of the sleeve member 180 can then be placed around and bonded to the outer surface of the attachment flange 116B of the head 110. The annular rib 116C can be used to locate the terminal edge of the sleeve member 180.

According to some embodiments, the annular seals formed between the sleeve member 180 and the attachment flange 156 and between the sleeve member 180 and the attachment flange 116B are substantially airtight.

The annular seals may be formed between the sleeve member 180 and the attachment flange 156 and the attachment flange 116B by techniques other than or in addition to heat welding, such as using adhesive.

Assembly of the inhalation device 100 can further include mounting the valve flap 122A on the body 112 by any suitable method such as heat staking. The mouthpiece 136 is mounted on the body 112 by pushing the hinge projections 142 down until they snap into engagement with the holes 126. The base 150 is completed by pushing the cover member 160 onto the ring member 152 such that the coupling rib 154A seats in the groove 164A.

According to some embodiments, the device 100 could be sterilized by any suitable method following assembly.

The sleeve member 180 is formed of a flexible plastic tube or sheet material. According to some embodiments, the sleeve material is durable and air impervious. According to some embodiments, the sleeve member 180 is formed of a polymeric material which can include an anti-static component. According to some embodiments, the sleeve member 180 is formed of a polymeric film having a thickness in the range of from about 4 to 8 mil. According to some embodiments, the sleeve member 180 is formed of a polymeric film having a thickness in the range of from about 4 to 6 mil.

According to some embodiments, the sleeve member 180 is formed of low density polyethylene (LDPE). According to some embodiments, the sleeve member 180 is formed of LDPE loaded, blended, mixed or coated with a supplemental material that enhances the anti-static properties of the LDPE, such as an olefin grade polyether polypropylene co-polymer (e.g., Sanyo Pelestat™)

According to some embodiments, the sleeve member 180 is formed of material (e.g., LDPE with anti-static enhancement) having a surface resistivity of $1 \times 10^{12}$ Ohms/square or less as measured according to ASTM D257-07 (*Standard Test Methods for DC Resistance or Conductance of Insulating Materials*) and, according to some embodiments, of between $1 \times 10^9$ and $1 \times 10^{12}$ Ohms/square according to ASTM D257-07.

The body 112 of the head 110 can be formed of any suitable material. According to some embodiments, the body 112 is unitarily molded. According to some embodiments, the body 112 is formed of a rigid or semi-rigid polymeric material. According to some embodiments, the body 112 is formed of high density polyethylene (HDPE). According to some embodiments, the head 110 is formed of polymer loaded, blended, mixed or coated with a supplemental material that enhances the anti-static properties of the polymer, such as an olefin grade polyether polypropylene co-polymer (e.g., Sanyo Pelestat™).

The mouthpiece 136 can be formed of any suitable material. According to some embodiments, the mouthpiece 136 is unitarily molded. According to some embodiments, the mouthpiece 136 is formed of a rigid or semi-rigid polymeric material. According to some embodiments, the mouthpiece 136 is formed of HDPE.

The valve flaps 122A, 139F can be formed of any suitable flexible, resilient material. According to some embodiments, the valve flaps 122A, 139F are unitarily molded. According to some embodiments, the valve flaps 122A, 139F are formed of TPE or silicone rubber.

The ring member 152 of the base 150 can be formed of any suitable material. According to some embodiments, the ring member 152 is unitarily molded. According to some embodiments, the ring member 152 is formed of a rigid or semi-rigid polymeric material. According to some embodiments, the ring member 152 is formed of HDPE. According to some embodiments, the ring member 152 is formed of polymer loaded, mixed or coated with a supplemental material that enhances the anti-static properties of the polymer, such as an olefin grade polyether polypropylene co-polymer (e.g., Sanyo Pelestat™).

The cover member 160 can be formed of any suitable material. According to some embodiments, the cover member 160 is unitarily molded. According to some embodiments, the cover member 160 is formed of a material that is less rigid and/or less hard than the ring member 152. According to some embodiments, the cover member 160 is formed of an elastomeric material. According to some embodiments, the cover member 160 is formed of a thermoplastic elastomer (TPE) or silicone. According to some embodiments, the cover member 160 is formed of an olefin grade polyether polypropylene co-polymer (e.g., Sanyo Pelestat™), or equivalent. According to some embodiments, the cover member 160 is formed of silicone rubber. According to some embodiments, the cover member 160 is formed of an elastomer loaded, blended, mixed or coated with a supplemental material that enhances the anti-static properties of the elastomer, such as an olefin grade polyether polypropylene co-polymer (e.g., Sanyo Pelestat™) or equivalent.

According to some embodiments, each of the foregoing components may be formed a material or materials that can be easily and readily sterilized by conventional techniques without destroying the device 100 or rendering the device 100 unsuitable for further use.

According to some embodiments, the length L1 (FIG. 1) of the inhalation device 100 when in the open position with the mouthpiece 136 deployed as shown in FIG. 1 is in the range of from about 4 to 10 inches and, according to some embodiments in the range of from about 6 to 6.4 inches. According to some embodiments, the length L2 (FIG. 1) from the end wall 114 to the end wall 162 when the inhalation device 100 is in the open position in the range of from about 4 to 9 inches and, according to some embodiments in the range of from about 5 to 5.4 inches.

According to some embodiments, the total thickness or length L3 (FIG. 10B) of the inhalation device 100 when in the closed position with the mouthpiece 136 stored as shown in FIG. 10 is in the range of from about 1.0 to 3.0 inches and, according to some embodiments in the range of from about 1.45 to 1.55 inches.

According to some embodiments, the outer diameter D1 (FIG. 4) of the inhalation device 100 is in the range of from about 2 to 5 inches and, according to some embodiments in the range of from about 2.8 to 3.5 inches.

According to some embodiments, the volume of the chamber 102 of the inhalation device 100 when the device 100 is fully open is in the range of from about 200 to 800 ml and, according to some embodiments in the range of from about 375 to 410 ml.

The inhalation system 10 may be used as follows according to methods of the present invention. Initially, the inhalation device 100 may be placed in the closed position of FIG. 10B so that it is compact for transport, storage or the like. With the device 100 in the open position and the dispenser 15 removed from the device 100, the user pushes the head 110 and the base 150 axially together such that the sleeve member 180 is captured therebetween and enveloped by the components 110, 150. According to some embodiments, the sleeve member 180 is fully enveloped by the head 110 and the base 150 in the closed position. According to some embodiments, the user may twist or rotate the head 110 and the base 150 relative to one another about the lengthwise axis as the user axially converges the head 110 and the base 150 in order to provide a helical lay or fold of the sleeve member 180 into the cavity defined between the head 110 and the base 150 when the device is in the closed position. The sleeve member 180 may have a configuration or material memory tending to direct the sleeve member 180 to follow the helical path or fold pattern. FIG. 10A shows the inhalation device 100 in a partially closed, collapsed or compressed position. The head 110 and the base 150 are pushed together until the annular rib 116C of the head 110 seats in and interlocks with the latch groove 152B in the interior surface of the ring member 152 to releasably retain the device 100 in the closed position. The mouthpiece 136 is folded down and latched in its stored position by engagement between the latch tab 128 and the front edge of the mouthpiece 136.

When the user desires to administer a dose of the medication from the MDI unit 20, the user may prepare the dispenser 15 as needed. For example, the user may shake the dispenser 15 and remove the cap 46C from the dispensing section 46.

To open the inhalation device 100, the user may press the tabs 152C axially away from the head 110 while pushing the end wall 162 of the base 150 toward the head 110. For example, the user may push forwardly on the end wall 162 with her thumbs while simultaneously pulling rearwardly on the tabs 152C with her fingers (or the placements and motions of the thumb and fingers may be reversed). In doing so, the user deflects or warps the ring member 152 to loosen or release the engagement between the coupling features 152B, 116C while simultaneously pushing the head 110 out from the base 150. With the head 110 and base 150 now disengaged, the user can pull the head 110 and base 150 away from one another along the longitudinal axis A-A to expand the sleeve member 180 into the deployed position of FIG. 2, thereby drawing a volume of air into the chamber 102. The mouthpiece 136 is folded out into the deployed position (FIG. 8), including forcing the mouthpiece 136 out of engagement between the latch tab 128, and further forcing the latch features 130 and 140 into engagement. Other methods or mechanisms may be used and provided for retaining the mouthpiece 136 in the open and closed positions.

The dispensing section 46 of the dispenser 15 is forced into the port 104 as shown in FIG. 12. The elastomeric sealing flange 166 grips the dispensing section 46 to hold the dispenser 15 in place on the base 150. According to some embodiments, the sealing flange 166 forms an airtight or highly air flow restricted seal about the dispensing section 46.

The patient P places the mouthpiece 136 in her mouth (as shown in FIG. 1; for example) and depresses the aerosol canister 22 to discharge and inject the dose D of medication into the chamber 102 through the dispensing section 46. The device 100 may be otherwise oriented. For example, the device 100 may be rotated 180 degrees about its lengthwise axis as compared to the position shown in FIG. 1. The dose D mixes with the air in the chamber 102 and is dispersed into a nonconcentrated or dilute dispersion suspended in the air as an air and medication mixture M. The gaseous pressure under which the medication was stored in the canister 22 is dissipated in the chamber 102 and the medication is dispersed in nonpressurized form (i.e., at ambient pressure). The one-way valve 122 is closed by default and may serve to prevent the premature escape of the dose D or the mixture M from the chamber 102 and to prevent the patient from exhaling into the chamber 102.

With the inhalation device 100 charged with the mixture M as described above, the patient P can slowly inhale the mixture M from the device 100 through the mouthpiece 136 into the patient's breathing passages and lungs. As the air volume is inhaled from the chamber 102, ambient air is drawn into the chamber 102 by the induced vacuum through a leak path defined between the dispensing section 46 and the inlet opening 104 of the sealing flange 166. The patient P may support the base 150 with her hand to prevent sagging of the base 150 that would otherwise tend to cause the sleeve member 180 to collapse under the weight of the base 150. The patient P may also support the head 110 with a hand. In some embodiments, the patient's inhalation suction draws the base 150 and the head 110 together. According to some embodiments, the base 150 and the head 110 are not forced together other than by the inhalation force, so that in order to collapse the breathing chamber, the patient must exert sufficient negative pressure within the chamber 102 to move the base 150 to the head 110 solely by negative thoracic pressure without mechanical or manual assistance.

If desired, a face mask 70 (FIG. 12) can be installed on the mouthpiece 136. The mask 70 can be fitted onto the patient's face (e.g., to cover both the patient's nose and mouth) and the delivery procedure can otherwise be executed in the same manner as described hereinabove. The blowback relief valve 139 will be located outside of the face mask 70.

During the inhalation step, the one-way valve 122 permits the mixture M to be drawn out of the inhalation device 100 while preventing air from being blown into the chamber 102 in the event the patient P exhales into the mouthpiece 136. Pressurization of the chamber 102 from patient exhalation might otherwise cause the medication to be blown out of the device 100.

The blowback relief valve 139 can facilitate more comfortable and effective use of the inhalation device 100 as well. If it is necessary or desired for the patient to exhale one or more times before fully inhaling the mixture M, the patient can exhale into the mouthpiece 136. The blowback relief valve 139 permits the exhaled air to exit the mouthpiece 136 without undue backpressure on the patient or breaching the valve 122 (i.e., inflow through the valve 122 into the chamber 102). The blowback relief valve 139 may allow users, such as children, to inhale and exhale normally without sensing any or an undue restriction or blockage. The valve 139 may be particularly useful in the case of pediatric subjects or elderly patients, in the event the patient coughs, and/or when the inhalation device 100 is used with a mask.

The latch features 130 and 140 (or other suitable features) help to retain the mouthpiece 136 in the deployed position during the preparation and administration steps. The guide wall 132 nests inside the passage 137 of the mouthpiece 136 to reduce or prevent leakage of the mixture M and/or ambient air through the interface between the body 112 and the mouthpiece 136. The guide wall 132 can also stabilize the mouthpiece 136.

The mouthpiece 136 may be configured to complement or fit a patient's mouth to facilitate dispersion of the medication throughout the patient's breathing passages. According to some embodiments, a face mask 70 (FIG. 12) may be detachably mounted on the mouthpiece 136 and used for oronasal or nasal inhalation. The mask may have a flexible sealing member with a slot therein of a size and shape to conformably receive and form a sealed engagement with the mouthpiece 136. The device 100 may be used with face masks of different sizes to accommodate patients of different sizes.

After the system 10 has been used to administer the dose D to the patient P, the dispenser 15 is withdrawn from the base 150 and the device 100 may be returned to its closed position as described above for storage and/or transport.

In order to facilitate cleaning of the inhalation device 100, the cover member 160 can be removed from the ring member 152 (by disengaging the groove 162A from the rib 154A) to provide convenient and effective access to the interior of the sleeve member 180, the head 110 and the base 150. The device 100 can be returned to its operational configuration by replacing the cover member 160 on the ring member 152.

The present invention can provide a portable therapeutic inhalation device that includes an expandable and collapsible medication receiving breathing bag or spacer chamber for allowing long and slow inhalation of the medication by the patient and that nevertheless is small, compact and lightweight, and may conveniently be carried about, stored and transported when not in use. The inhalation device may be compactly stored so that the device may conveniently and safely be carried about in a pocket or a purse. The device can be reusable and easily cleanable.

In use, the device of the invention provides an expandable and collapsible breathing chamber of relatively large volume for reception of a medication from an aerosol canister and for uniform dispersion of the medication in relatively dilute and nonpressurized form within the chamber. According to some embodiments, in order to inhale the dispersed medication from the chamber, the patient must exert a negative thoracic pressure at the inhalation member in order to collapse the breathing chamber and induce the flow of medication from the chamber into the patient's breathing passages. This in turn encourages and promotes a long and slow inspiration period in order to obtain maximum utilization of the medication and maximum efficacy from the therapeutic exercise.

The inhalation device 100 is adapted for use with dispensers having various form factors and, in particular, dispensers including an MDI unit operably mounted in a holder of the type commonly referred to as a boot. This aspect of the inhalation device may be advantageous in that it enables the user to enjoy features of the holder. In particular, according to some embodiments, the holder includes an integral dose counter 50. By dispensing the dose from the MDI unit 20 using the holder 40 (through the inhalation device 100), the user can keep track of the number of doses dispensed from or remaining in the MDI unit 20.

The valve 122 can prevent the user from blowing the medication out of the chamber 102. Also, the one-way valve 122 and the trap structure 138 can prevent entry of foreign objects into the device 100 when the device 100 is carried in a pocket or purse, and thereby prevent subsequent inhalation of any such foreign object by the patient.

The medication stored in and delivered from the MDI unit 20 via the device 100 may be any suitable and desired inhalation medication. Exemplary medications include ProAir® HFA (albuterol sulfate), Symbicort® (budesonide/formoterol fumarate dihydrate; includes counter), Advair® HFA (fluticasone propionate and salmeterol; includes counter), and Proventil® HFA (albuterol sulfate).

The method of attaching the sleeve member 180 to the base 150 as described herein with reference to FIGS. 11A and 11B can provide a number of advantages. The sleeve member 180 can be more easily, cost-effectively and reliably welded to the outer diameter of the ring member 152. The weld location is placed outside of the chamber 102 so that it does not present a surface that may be difficult to clean. The number of pieces for assembly of the base 150 and the sleeve member 180 is relatively few. The cover member 160, when mounted on the ring member 152, can provide mechanical strain relief between the sleeve member 180 and the ring member 152 by capturing the transitional section 183 of the sleeve member 180.

The size and volumetric capacity of the chamber 102 may be adjusted to meet the varying needs of various patients by producing the inhalation device of the invention in different diameters and/or with collapsible sleeve members 180 of various lengths and diameters.

With reference to FIGS. 13-23, an inhalation device or spacer 200 according to further embodiments of the present invention is shown therein. The inhalation device 200 may be used in conjunction with the MDI unit 20 (FIGS. 1, 12 and 14), for example, to form an inhalation system 25 (FIG. 14) to deliver medication from the dispenser 15 in an air diluted and nonpressurized form to the oronasal breathing passages of a human patient as discussed above with regard to the inhalation device 100. In the case of the inhalation device 200, the dispenser 15 can be actuated to inject a prescribed or predetermined metered dose of the medication into a chamber 202 defined by the inhalation device 200, where the medication dose is mixed with air in the chamber 202 to form a dispersed, gaseous medicine mixture. A patient can then inhale the mixture from the inhalation device 200 through a mouthpiece portion 240 of the inhalation device 200.

Figure 23:
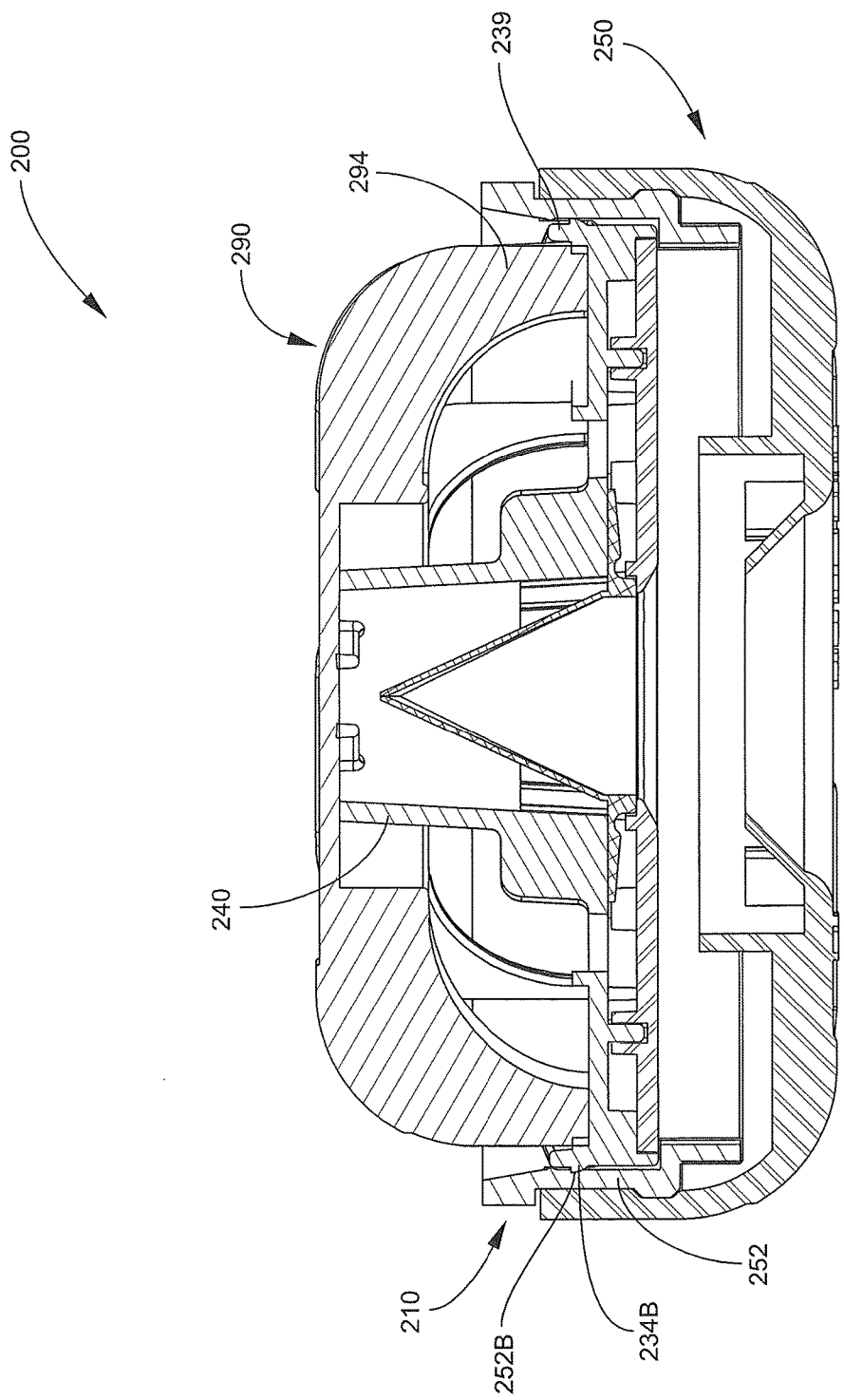
FIG. 23 is a cross-sectional view of the inhalation device of FIG. 13 in a closed, collapsed position.

Advantageously, the inhalation device 200 can be collapsed into a relatively compact form factor when not in use, as shown in FIG. 23.

With reference to FIGS. 13-17, the inhalation device 200 has a longitudinal axis A-A and includes an outlet end member, assembly, unit or head 210 (hereinafter, the head 210), an inlet end member 250 (hereinafter, the base 250), a pliable, flexible bag or sleeve member 280, and a lid or head cover member 290. The head 210, the base 250, and the sleeve member 280 collectively define the chamber 202.

The base 250 corresponds to and may be substantially identical to the base 150. The base 250 includes an inlet opening or aerosol injection port 204 (FIG. 16) communicating with the chamber 202 to receive the dispenser 15 as discussed above with regard to the base 150.

The sleeve member 280 corresponds to and may be substantially identical to the sleeve member 180. The sleeve member 280 can be joined to the base 250 in the same manner as described above for the sleeve member 180 and the base 150.

The head 210 includes a valve member 220, a mouthpiece member 230, and a support ring or back plate 244. The back plate 244 is affixed to the mouthpiece member 230 with the valve member 220 interposed therebetween to form a unitary assembly. According to some embodiments, the back plate 244 is permanently affixed to the mouthpiece member 230 so that the two cannot be separated and the valve member 220 cannot be removed therefrom without damaging one or more of the components 220, 230, 244. That is, the head 210 and the components 220, 230, 244 are not serviceable or replaceable.

Figure 16:
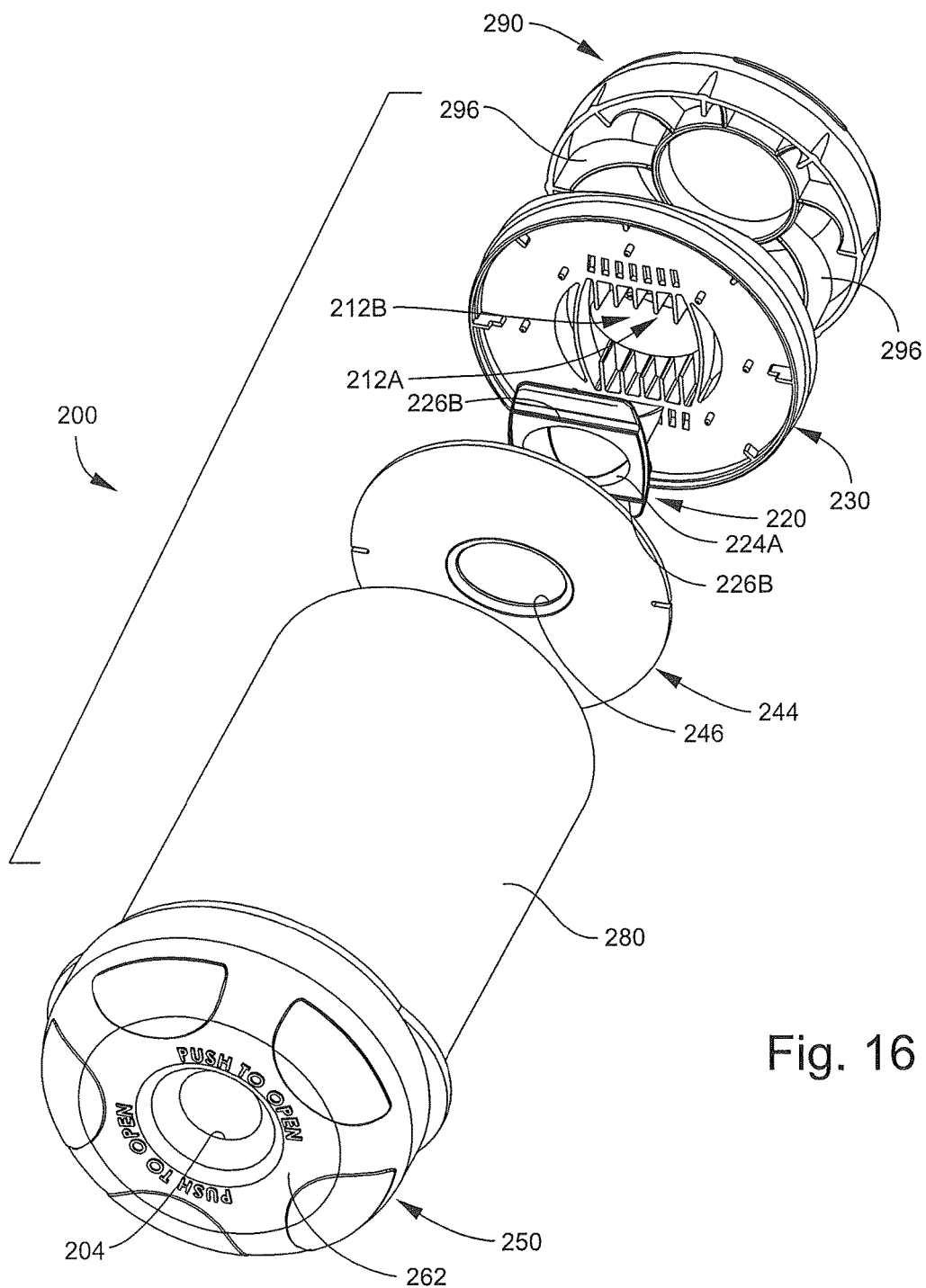
FIG. 16 is an exploded, rear, bottom perspective view of the inhalation device of FIG. 13.
Figure 17:
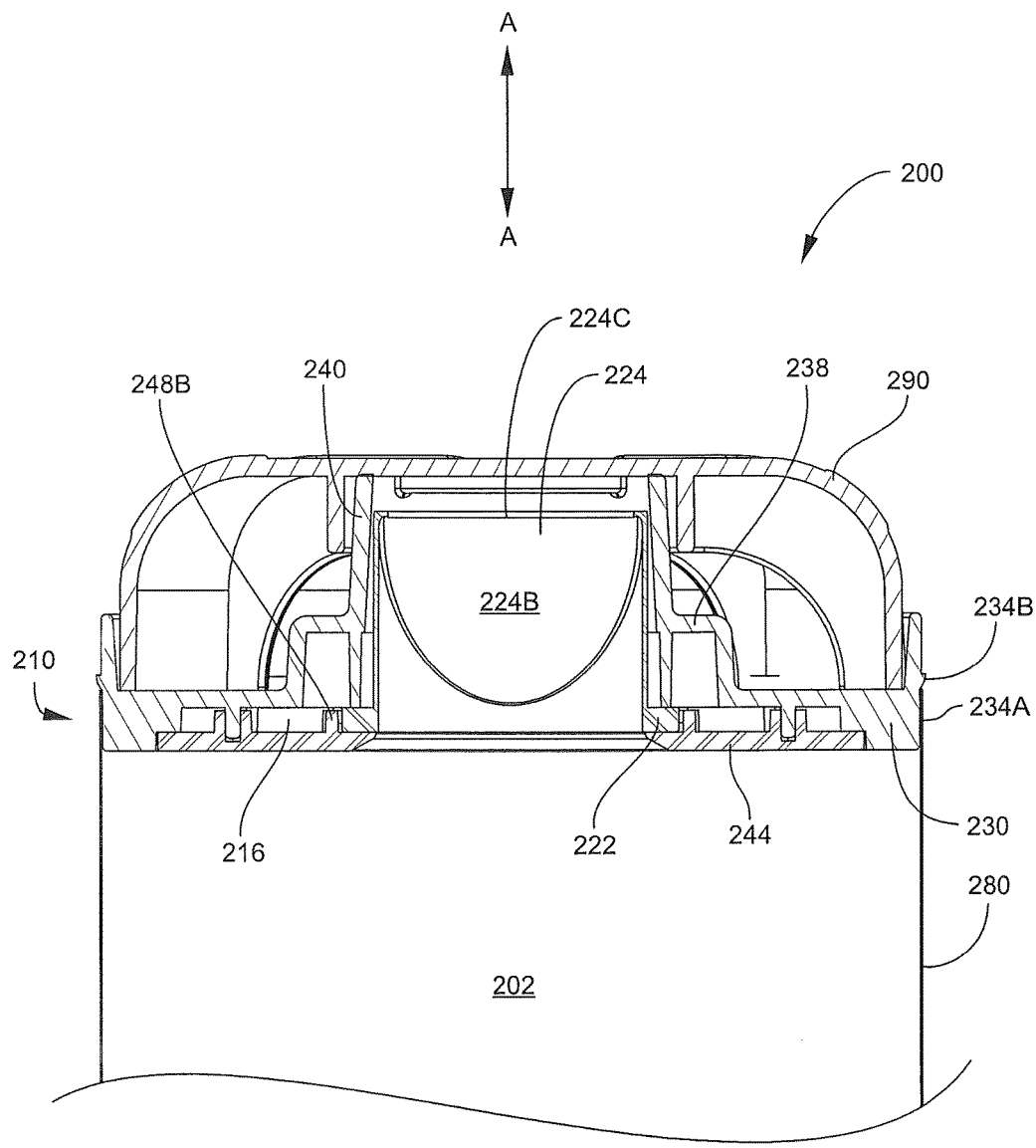
FIG. 17 is a fragmentary, cross-sectional view of the inhalation device of FIG. 13 taken along the line 17-17 of FIG. 14.
Figure 19:
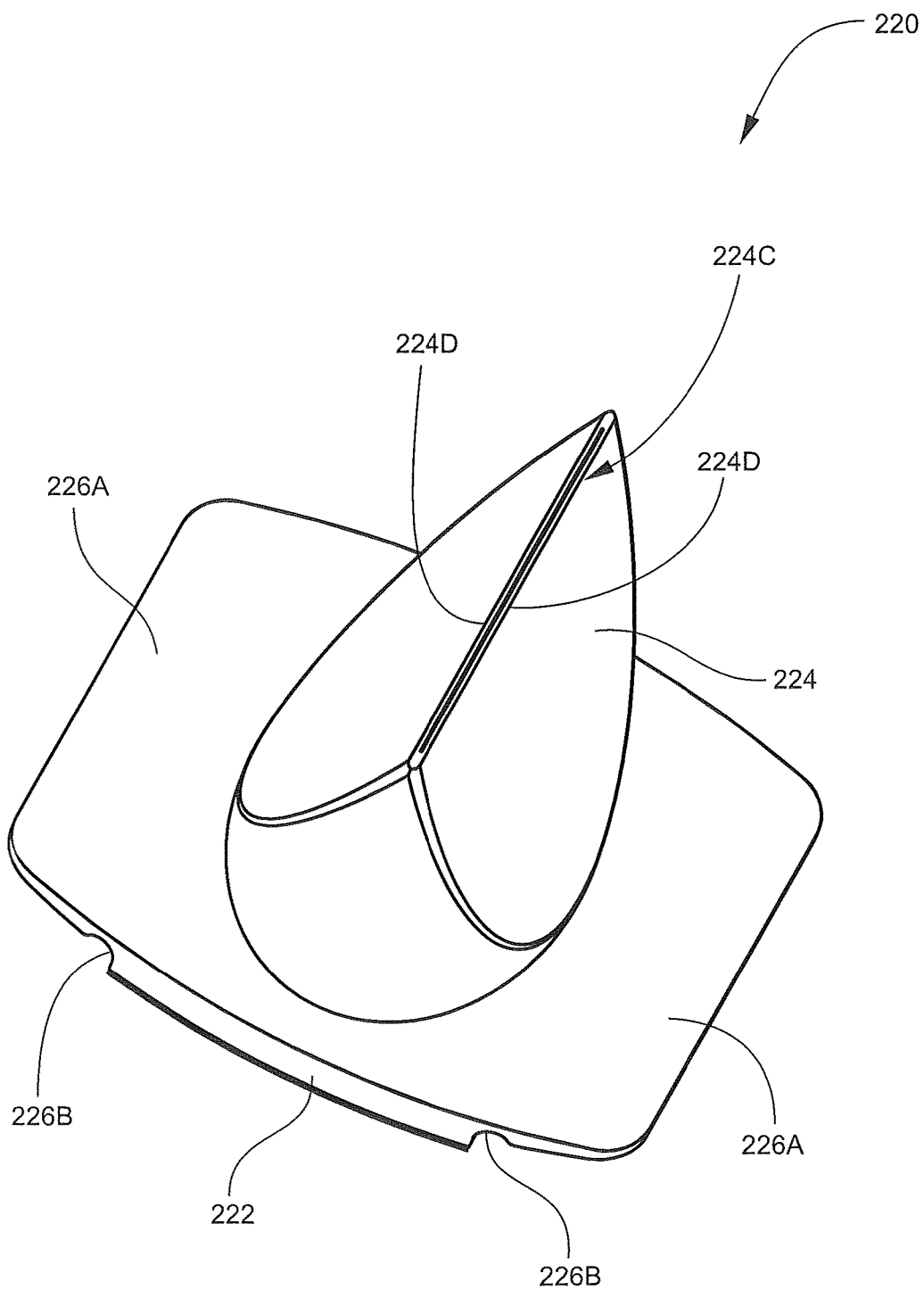
FIG. 19 is a top perspective view of a valve member forming a part of the inhalation device of FIG. 13.

With reference to FIGS. 16, 17 and 19, the valve member 220 includes a base portion 222, an integral inhalation valve 224, and opposed, integral side valve flaps 226A. Hinge grooves 226B are defined in the base portion 222 between the base portion 222 and the flaps 226A. According to some embodiments, the valve member 220 is monolithic.

The inhalation valve 224 is a one-way, self-sealing valve configured to permit air to flow out from the chamber 202 through the mouthpiece portion 240. The valve 224 includes an entrance opening 224A, an axially opposing a slit 224C (defined by opposed edges 224D), and an axially extending through passage 224B (FIG. 17) fluidly connecting the opening 224B and the slit 224C. Upon application of a sufficient pressure differential across the slit 224C, the edges 224D will separate to form an enlarged opening at the slit 224C through which an inhalation flow can pass. According to some embodiments and as shown, the inhalation valve 224 is a duckbill valve.

The inhalation valve 224 may be formed of any suitable flexible, resilient material. According to some embodiments, the inhalation valve 224 is unitarily molded and, in some embodiments, is monolithic. According to some embodiments, the inhalation valve 224 is formed of TPE or silicone rubber.

With reference to FIGS. 14-17 and 20A, the mouthpiece member 230 includes an end wall portion 232, an annular side wall portion 234, mounting posts 236A, locator tabs 236B, a fluid connector portion 238, an annular front flange 239, and the mouthpiece portion 240. Forwardly directed exhaust ports 218 are defined in an axial end face 232A (FIG. 18) of the end wall portion 232.

The side wall portion 234 includes an annular attachment surface or portion 234A (corresponding to the attachment portion 116B of the head 110) and an annular rib 234B (corresponding to the rib 116C of the head 110). The front end of the sleeve member 280 is affixed to the attachment portion 234A in the same manner as discussed above with regard to the attachment portion 116B and the sleeve member 180 (e.g., bonded by heat welding).

The upstanding flange 239 extends forwardly from the end wall portion 232 and defines a front cavity 239A. Opposing cutouts or slots 239B (FIG. 14) are defined in the flange 239.

The fluid connector portion 238 includes a plurality of partition walls 238A each having a lower edge 238B and defining connecting passages 214A.

The mouthpiece portion 240 defines a through passage 212A (FIG. 16) terminating at an inlet opening 212B and an opposed outlet opening 212C. A trap structure, filter or grill 242 may be provided in the passage 212A (e.g., at or proximate the outlet opening 212C). The trap structure 242 may serve to inhibit or prevent the entry of foreign objects or debris into the mouthpiece 240 as well as to ensure that the valve member 220, if all or a portion of it were to become detached from between the mouthpiece member 230 and the back plate 244, is not inhaled by the patient.

The mouthpiece member 230 can be formed of any suitable material. According to some embodiments, the mouthpiece member 230 is unitarily molded. According to some embodiments, the mouthpiece member 230 is monolithic. According to some embodiments, the mouthpiece member 230 is formed of a rigid or semi-rigid polymeric material. According to some embodiments, the mouthpiece member 230 is formed of high density polyethylene (HDPE). According to some embodiments, the mouthpiece member 230 is formed of polymer loaded, blended, mixed or coated with a supplemental material that enhances the anti-static properties of the polymer, such as an olefin grade polyether polypropylene co-polymer (e.g., Sanyo Pelestat™).

The back plate 244 (FIGS. 15 and 16) includes a wafer-shaped body 244A, post slots 244B, edge slots 244C and a through opening 246. The back plate 244 further includes integral locator ribs 248A, 248B defining a valve member locator cavity 248C complementary to the base portion 222. The back plate 244 may be formed of the same or different materials than the mouthpiece member 230. According to some embodiments, the back plate 244 is unitarily molded. According to some embodiments, the back plate 244 is monolithic.

The cover member 290 (FIGS. 15 and 16) includes an end wall 292 and an annular sidewall 294 depending therefrom. The cover member 290 may further include integral reinforcement ribs 296 on its inner side. The cover member 290 can be formed of any suitable material. According to some embodiments, the cover member 290 is unitarily molded. According to some embodiments, the cover member 290 is formed of a rigid material such as a thermoplastic, which may be harder than the material of the cover member 160. In some embodiments, the cover member 290 is formed of high density polyethylene (HDPE). According to some embodiments, the cover member 290 is formed of a material that is less rigid and/or less hard than the mouthpiece member 230. According to some embodiments, the cover member 290 is formed of an elastomeric material. According to some embodiments, the cover member 290 is formed of a thermoplastic elastomer (TPE) or silicone. According to some embodiments, the cover member 290 is formed of an olefin grade polyether polypropylene co-polymer (e.g., Sanyo Pelestat™), or equivalent. According to some embodiments, the cover member 290 is formed of silicone rubber. According to some embodiments, the cover member 290 is formed of an elastomer loaded, blended, mixed or coated with a supplemental material that enhances the anti-static properties of the elastomer, such as an olefin grade polyether polypropylene co-polymer (e.g., Sanyo Pelestat™) or equivalent.

Figure 20A:
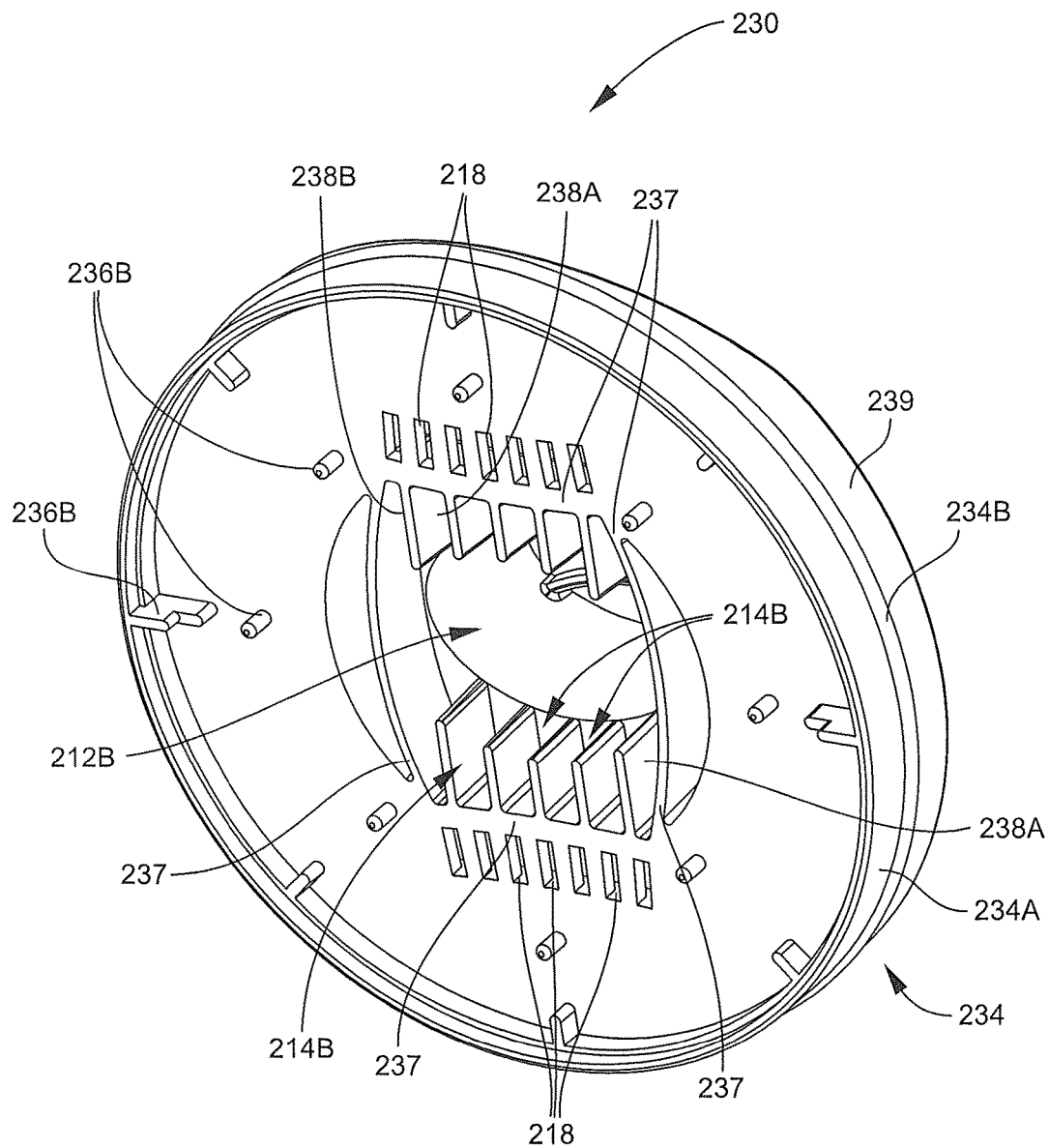
FIG. 20A is a bottom perspective view of a mouthpiece member forming a part of the inhalation device of FIG. 13.
Figure 20B:
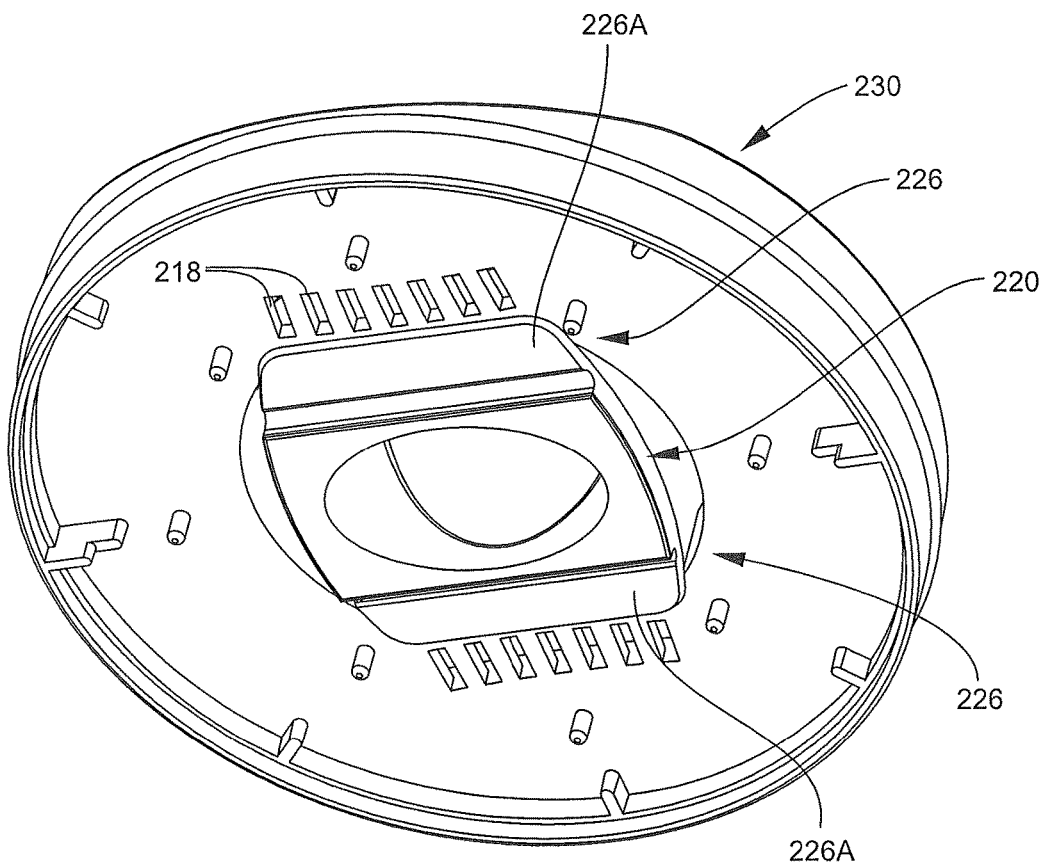
FIG. 20B is a bottom perspective view of the mouthpiece member of FIG. 20A with the valve member mounted therein.

The inhalation device 200 can be assembled as follows. The valve member 220 is inserted and mounted on the rear side of the mouthpiece member 230, as illustrated in FIGS. 20A and 20B such that the inhalation valve 224 is received in the mouthpiece passage 212A and the valve flaps 226A cover valve ports 214B at the rear ends of the connecting passages 214A. The back plate 244 is secured to the rear side of the mouthpiece member 230 such that the valve member base 222 is received in the valve locator cavity 248C. More particularly, the posts 236A are received in the slots 244B and the tabs 236B are received in the slots 244C. The posts 236A may be secured in the slots 244B by heat staking, adhesive, mechanical interlock, interference fit, or any other suitable means. The assembled head 210 is affixed to the sleeve member 280 as described above.

The valve flaps 226A and valve seat portions 237 (FIG. 20A) of the mouthpiece member 230 engaged by the valve flaps 226A form respective laterally opposed one-way exhalation or blowback relief valves 226. More particularly, a valve port 214B is defined at the rearward or inward end of each connecting passage 214A. Each valve flap 226A is pressed against its valve seat portion 237 such that it fluidly blocks or seals the valve ports 214B on its side of the mouthpiece portion 240.

Figure 18:
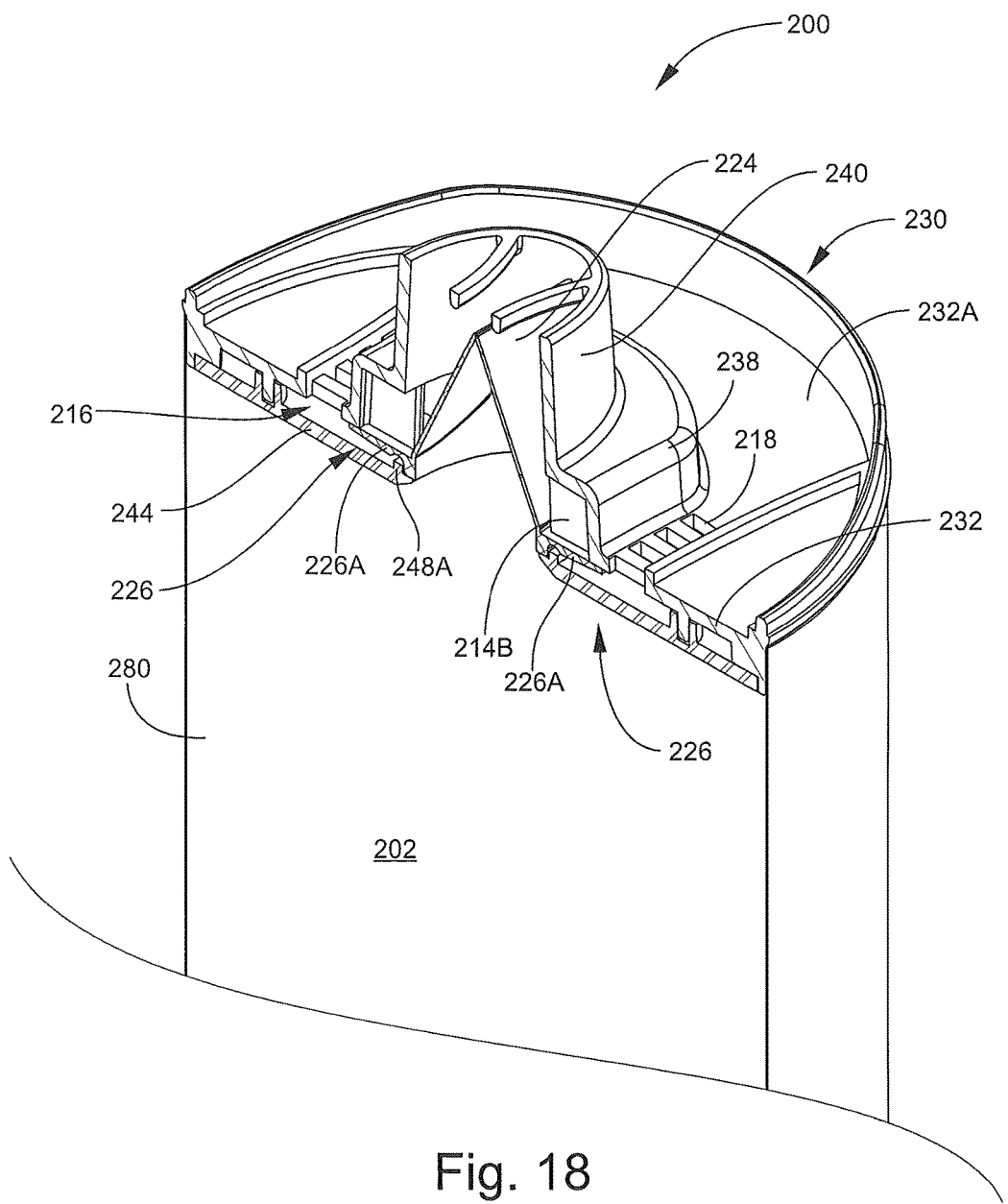
FIG. 18 is a fragmentary, perspective, cross-sectional view of the inhalation device of FIG. 13 taken along the line 18-18 of FIG. 14.

Furthermore, the back plate 244 and the mouthpiece member 230 define an integral fluid conduit or plenum 216 therebetween (FIGS. 17 and 18). The conduit 216 fluidly communicates with the exhaust ports 218.

The inhalation system 25 may be used as follows according to methods of the present invention. Initially, the inhalation device 200 may be placed in the closed position of FIG. 23 so that it is compact for transport, storage or the like. To attain the closed position from the open position, the MDI unit 20 is removed (if necessary) from the device 200, and the user pushes the head 210 and the base 250 axially together such that the sleeve member 280 is captured therebetween and enveloped by the components 210, 250. According to some embodiments, the sleeve member 280 is fully enveloped by the head 210 and the base 250 in the closed position. According to some embodiments, the user may twist or rotate the head 210 and the base 250 relative to one another about the lengthwise axis as the user axially converges the head 210 and the base 250 in order to provide a helical lay or fold of the sleeve member 280 into the cavity defined between the head 210 and the base 250 when the device is in the closed position. The sleeve member 280 may have a configuration or material memory tending to direct the sleeve member 280 to follow the helical path or fold pattern. The head 210 and the base 250 are pushed together until the annular rib 234B of the head 210 seats in and interlocks with the latch groove 252B in the interior surface of the ring member 252 to releasably retain the device 200 in the closed position.

For storage and handling, the cover member 290 can be temporarily mounted on the head 210 as shown in FIG. 23. The lower edge portion of the cover member side wall 294 is captured by interference fit within the flange 239. According to some embodiments, the cover member 290, when mounted on the mouthpiece member 230, provides a substantially airtight seal therebetween (FIG. 23). The flange cutouts 239B can facilitate removal of the cover member 290 by providing access to gripping locations for the user.

When the user desires to administer a dose of the medication from the MDI unit 20, the user may prepare the dispenser 15 as needed. For example, the user may shake the dispenser 15 and remove the cap 46C (FIG. 12) from the dispensing section 46.

To open the inhalation device 200, the user may press the tabs 252C (FIG. 15) axially away from the head 210 while pushing the end wall 262 (FIG. 16) of the base 250 toward the head 210 as described above with regard to the inhalation device 100. In this manner, the head 210 can be released from the base 250 and the head 210 and base 250 can be pulled apart to extend the sleeve member 280. The cover member 290 is removed before or after opening the device 200.

The dispensing section 46 of the dispenser 15 is mounted on the base 250 as described above with regard to the device 100.

The patient places the mouthpiece portion 240 in her mouth and depresses the aerosol canister 22 to discharge and inject the dose of medication into the chamber 202 through the dispensing section 46. The dose mixes with the air in the chamber 202 and is dispersed into a nonconcentrated or dilute dispersion suspended in the air as an air and medication mixture. The gaseous pressure under which the medication was stored in the canister 22 is dissipated in the chamber 202 and the medication is dispersed in nonpressurized form (i.e., at ambient pressure). The one-way inhalation valve 224 is closed by default and may serve to prevent the premature escape of the dose or the mixture from the chamber 202 and to prevent the patient from exhaling into the chamber 202.

With the inhalation device 200 charged with the mixture as described above, the patient can slowly inhale the mixture from the device 200 through the mouthpiece portion 240 into the patient's breathing passages and lungs. As the air volume is inhaled from the chamber 202, ambient air may be drawn into the chamber 202 by the induced vacuum through a leak path defined between the dispensing section 46 and the inlet opening 204. The patient may support the base 250 with her hand to prevent sagging of the base 250 that would otherwise tend to cause the sleeve member 280 to collapse under the weight of the base 250. The patient may also support the head 210 with a hand. In some embodiments, the patient's inhalation suction draws the base 250 and the head 210 together. According to some embodiments, the base 250 and the head 210 are not forced together other than by the inhalation force, so that in order to collapse the breathing chamber, the patient must exert sufficient negative pressure within the chamber 202 to move the base 250 to the head 210 solely by negative thoracic pressure without mechanical or manual assistance.

After the system 25 has been used to administer the dose to the patient, the dispenser 15 is withdrawn from the base 250 and the device 200 may be returned to its closed position as described above for storage and/or transport.

Figure 21:
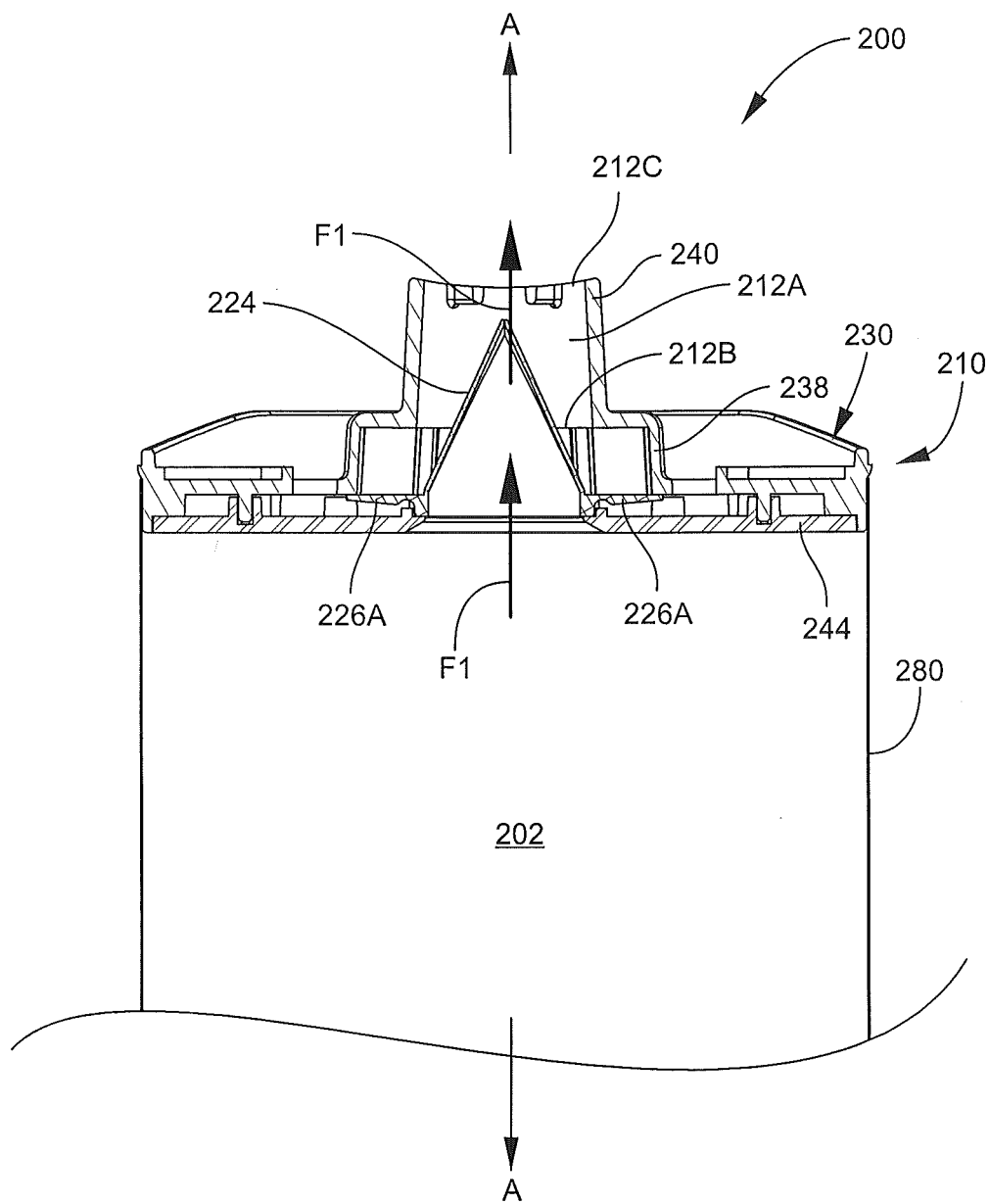
FIG. 21 is a fragmentary, cross-sectional view of the inhalation device of FIG. 13 taken along the line 18-18 of FIG. 14 illustrating an inhalation flow through the inhalation device.
Figure 22:
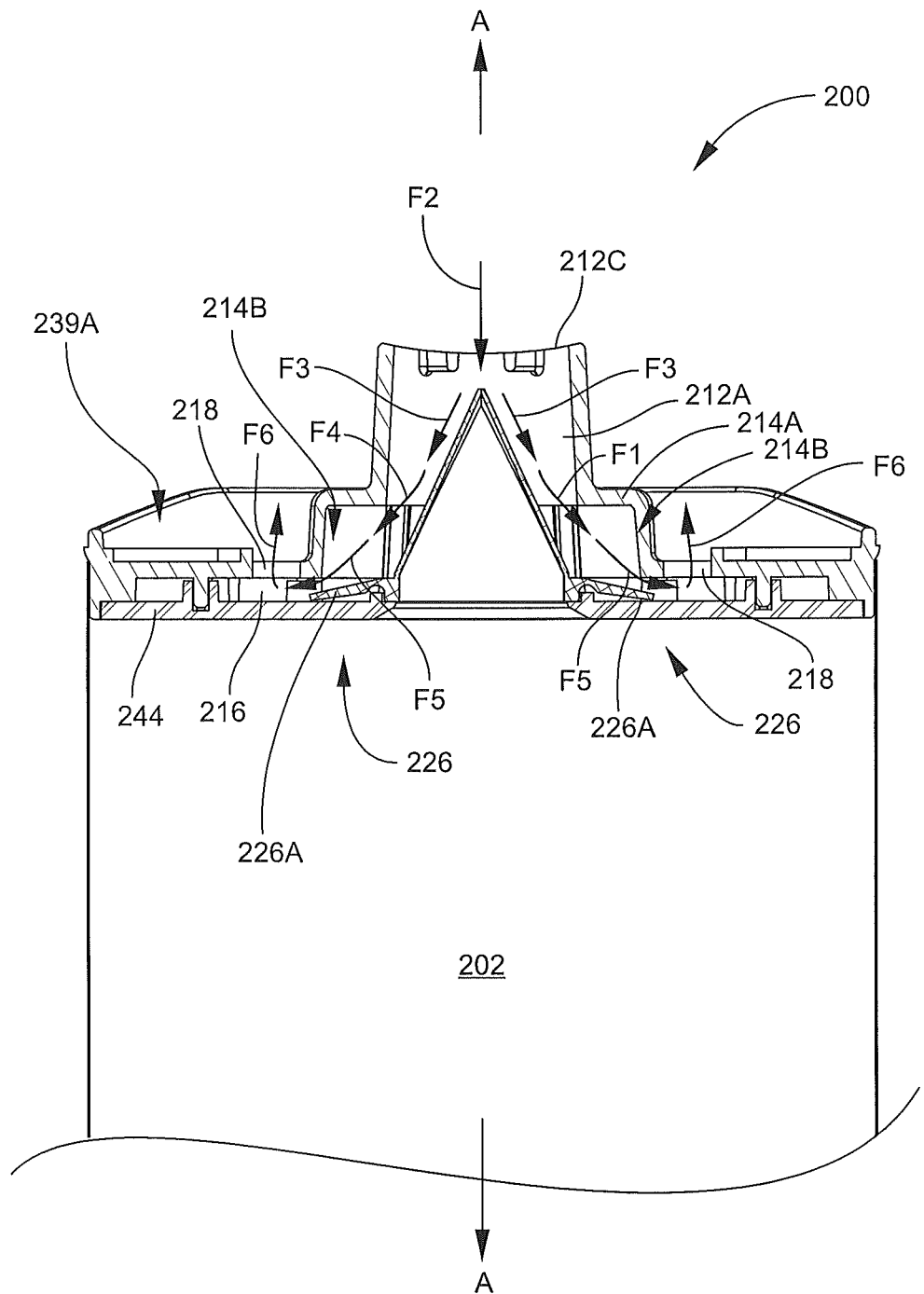
FIG. 22 is a fragmentary, cross-sectional view of the inhalation device of FIG. 13 taken along the line 18-18 of FIG. 14 illustrating an exhalation flow through the inhalation device.

During the inhalation step, the one-way inhalation valve 224 permits a flow F1 of the mixture to be drawn out of the inhalation device 200 as shown in FIG. 21. The one-way blowback relief valves 226 prevent ambient air from being drawn into the inhalation airstream through the valve ports 214B.

Meanwhile, if the patient exhales into the mouthpiece portion 240, the exhalation flow is prevented by the one-way inhalation valve 224 from being blown into the chamber 202 and is instead redirected through the head 210. More particularly and with reference to FIG. 22, an exhalation flow of sufficient pressure enters through the mouthpiece outlet opening 212C (indicated as flow F2), flows around the inhalation valve 224 (flow F3), flows into and through the connecting passages (flow F4), deflects the valve flaps 226A rearwardly away from their valve seats 237, flows through the temporarily open valve ports 214B (flow F5), flows through the conduit 216 (flow F5 continued), and finally flows forwardly (i.e., axially in the direction of the patient) out of the head 210 through the exhaust ports 218 (flow F6). The valve flaps 226A may bend or deflect at the hinge grooves 226B (which act as living hinges) and/or along the flap bodies.

It will be appreciated that the exhaust valves 226 can provide the advantages and functionality as discussed above with regard to the blowback relief valve 139.

Because the exhaust ports 218 are located on the front side of the end wall 232 and are surrounded by the front flange 239 in the front cavity 239A, the risk that the patient will inadvertently block the exhaust ports 218 (e.g., with a finger) is greatly reduced. Also, the cover member 290 when installed will cover the exhaust ports 218 as well as the mouthpiece portion 240 to block intrusion by debris or objects that may interfere with the operation of the inhalation valve 224 or the blowback relief valves 226.

The mouthpiece portion 240 may be configured to complement or fit a patient's mouth to facilitate dispersion of the medication throughout the patient's breathing passages. If desired, a face mask (e.g., the face mask 70 of FIG. 12) can be installed on the mouthpiece portion 240. The mask 70 can be fitted onto the patient's face (e.g., to cover both the patient's nose and mouth) and the delivery procedure can otherwise be executed in the same manner as described hereinabove. It will be appreciated that the mask 70 will not interfere with the operation of the inhalation valve 224 or the exhaust valves 226.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention. Therefore, it is to be understood that the foregoing is illustrative of the present invention and is not to be construed as limited to the specific embodiments disclosed, and that modifications to the disclosed embodiments, as well as other embodiments, are intended to be included within the scope of the invention.

What is claimed is:

1. A collapsible inhalation device for use with a metered dose inhaler (MDI) dispenser, the MDI dispenser operable to dispense a dose of a medication therefrom, the inhalation device comprising:

an outlet end member including a mouthpiece;

an inlet end member including an inlet port and an MDI dispenser mount structure configured to receive and engage the MDI dispenser; and a tubular, pliable, collapsible sleeve member having first and second opposed ends attached to the inlet end member and the outlet end member, respectively;

wherein the inhalation device is positionable in each of an open position, wherein the outlet end member and the inlet end member are spaced apart and the sleeve member is extended such that the outlet end member, the inlet end member and the sleeve member define a chamber, and a closed position, wherein the sleeve member is collapsed and the outlet end member and the inlet end member are proximate one another and envelope the sleeve member; and wherein, when the inhalation device is in the open position with the MDI dispenser mounted in the MDI dispenser mount structure, a dose of the medication can be dispensed from the MDI dispenser into the chamber through the inlet port to mix with air in the chamber and thereby form a mixture of the air and the dose of the medication that can be inhaled by a patient from the chamber through the mouthpiece.

2. A collapsible inhalation device for use with a metered dose inhaler (MDI) dispenser, the MDI dispenser operable to dispense a dose of a medication therefrom, the inhalation device comprising:

an outlet end member including a mouthpiece;
an inlet end member including an inlet port and an MDI dispenser mount structure configured to receive and engage the MDI dispenser; and
a tubular, pliable, collapsible sleeve member having first and second opposed ends attached to the inlet end member and the outlet end member, respectively;
wherein the inhalation device is positionable in each of an open position, wherein the outlet end member and the inlet end member are spaced apart and the sleeve member is extended such that the outlet end member, the inlet end member and the sleeve member define a chamber, and a closed position, wherein the sleeve member is collapsed and the outlet end member and the inlet end member are proximate one another and envelope the sleeve member;
wherein, when the inhalation device is in the open position with the MDI dispenser mounted in the MDI dispenser mount structure, a dose of the medication can be dispensed from the MDI dispenser into the chamber through the inlet port to mix with air in the chamber and thereby form a mixture of the air and the dose of the medication that can be inhaled by a patient from the chamber through the mouthpiece;
wherein the inlet end member includes a ring member to which the sleeve member is affixed, and a cover member mounted on the ring member, wherein the cover member is removable from and replaceable on the ring member to provide access to the interior of the inhalation device for cleaning; and
wherein the cover member is formed of a first material including a resilient, deformable elastomer, and the ring member is formed of a second material more rigid than the first material.

3. The inhalation device of claim 2 wherein the ring member is formed of a rigid or semi-rigid material.

4. The inhalation device of claim 3 wherein the ring member is formed of high density polyethylene.

5. The inhalation device of claim 2 wherein the ring member is formed of a polymeric material blended and/or coated with a supplemental material that imparts an anti-static property to the polymeric material.

6. The inhalation device of claim 2 wherein the cover member is formed of a thermoplastic elastomer or silicone rubber.

7. The inhalation device of claim 2 wherein the cover member is formed of a polymeric material blended and/or coated with a supplemental material that imparts an anti-static property to the polymeric material.

8. The inhalation device of claim 2 wherein, when the inhalation device is in the closed position, the outlet end member and the inlet end member fully envelope the sleeve member.

9. The inhalation device of claim 2 wherein the MDI dispenser includes an MDI aerosol canister mounted in an MDI holder having a dispensing section, and the inlet port and the MDI dispenser mount structure are configured to receive and engage the dispensing section such that the dispensing section extends through the inlet port.

10. The inhalation device of claim 2 wherein the outlet end member includes a one-way inhalation valve that enables outflow of air from the chamber through the mouthpiece and prevents inflow of air into the chamber through the mouthpiece.

11. The inhalation device of claim 10 wherein the outlet end member includes a one-way blowback relief valve that enables outflow of air from the mouthpiece through the one-way blowback relief valve and prevents inflow of ambient air into the mouthpiece through the one-way blowback relief valve.

12. The inhalation device of claim 10 wherein the mouthpiece includes a grill configured to catch and prevent a component of the one-way inhalation valve from being inhaled through the mouthpiece.

13. The inhalation device of claim 2 wherein the sleeve member is substantially cylindrical when the inhalation device is in the open position.

14. The inhalation device of claim 2 wherein the sleeve member is formed of a polymeric film having a thickness in the range of from about 4 to 8 mil.

15. The inhalation device of claim 14 wherein the polymeric film has a thickness in the range of from about 4 to 6 mil.

16. The inhalation device of claim 2 wherein the sleeve member is formed of a low density polyethylene (LDPE) film.

17. The inhalation device of claim 16 wherein the LDPE film is an anti-static LDPE film having a surface resistivity of $1 \times 10^{12}$ Ohms/square or less as measured according to ASTM D257-07.

18. The inhalation device of claim 2 wherein the outlet end member includes a body and the mouthpiece is hingedly coupled to the body to rotate between an extended, deployed position and a retracted, stored position.

19. A method for administering a dose of a medication to a patient from a metered dose inhaler (MDI) dispenser, the method comprising:
a) providing a collapsible inhalation device including:
an outlet end member including a mouthpiece;
an inlet end member including an inlet port and an MDI dispenser mount structure configured to receive and engage the MDI dispenser; and
a tubular, pliable, collapsible sleeve member having first and second opposed ends attached to the inlet end member and the outlet end member, respectively;
wherein the inhalation device is positionable in each of an open position, wherein the outlet end member and the inlet end member are spaced apart and the sleeve member is extended such that the outlet end member, the inlet end member and the sleeve member define a chamber, and a closed position, wherein the sleeve member is collapsed and the outlet end member and the inlet end member are proximate one another and envelope the sleeve member;
b) placing the inhalation device in the open position;
c) mounting the MDI dispenser in the MDI dispenser mount structure; and thereafter;
d) dispensing a dose of the medication from the MDI dispenser into the chamber through the inlet port to mix with air in the chamber and thereby form a mixture of the air and the dose of the medication that can be inhaled by a patient from the chamber through the mouthpiece;
wherein the inlet end member includes a ring member to which the sleeve member is affixed, and a cover member mounted on the ring member, wherein the cover member is removable from and replaceable on the ring member to provide access to the interior of the inhalation device for cleaning; and
wherein the cover member is formed of a first material including a resilient, deformable elastomer, and the ring member is formed of a second material more rigid than the first material.

20. The method of claim 19 wherein, when the inhalation device is in the closed position, the outlet end member and the inlet end member fully envelope the sleeve member.

\* \* \* \* \*